(12) United States Patent
Eda et al.

(10) Patent No.: US 7,386,335 B2
(45) Date of Patent: Jun. 10, 2008

(54) BODY ACTIVITY MEASUREMENT DEVICE

(75) Inventors: Hideo Eda, Tokyo (JP); Yasufumi Kuroda, Tokyo (JP); Takanori Maesako, Osaka (JP); Katsuo Sugai, Osaka (JP)

(73) Assignee: National Institute of Information and Communications Technology, Tokyo (JP)

( * ) Notice: Subject to any disclaimer, the term of this patent is extended or adjusted under 35 U.S.C. 154(b) by 517 days.

(21) Appl. No.: 11/034,194

(22) Filed: Jan. 11, 2005

(65) Prior Publication Data

US 2005/0171435 A1 Aug. 4, 2005

(30) Foreign Application Priority Data

Jan. 14, 2004 (JP) .......................... P2004-007367

(51) Int. Cl.
*A61B 5/00* (2006.01)
*A61B 5/1455* (2006.01)

(52) U.S. Cl. .................. 600/323; 600/473; 600/476

(58) Field of Classification Search ............. 600/475, 600/477, 315, 323, 476, 473; 356/39–42
See application file for complete search history.

(56) References Cited

U.S. PATENT DOCUMENTS

| | | | |
|---|---|---|---|
| 5,218,529 A * | 6/1993 | Meyer et al. ............... | 702/28 |
| 5,803,909 A | 9/1998 | Maki et al. | |
| 6,321,110 B1 * | 11/2001 | Ito et al. ..................... | 600/476 |
| 6,397,099 B1 * | 5/2002 | Chance ...................... | 600/473 |
| 6,549,795 B1 * | 4/2003 | Chance ...................... | 600/340 |
| 6,577,884 B1 * | 6/2003 | Boas .......................... | 600/310 |
| 6,615,065 B1 * | 9/2003 | Barrett et al. ............... | 600/340 |
| 6,731,967 B1 * | 5/2004 | Turcott ....................... | 600/407 |
| 6,889,075 B2 * | 5/2005 | Marchitto et al. .......... | 600/473 |
| 6,901,284 B1 | 5/2005 | Maki et al. | |
| 6,907,280 B2 * | 6/2005 | Becerra et al. .............. | 600/407 |
| 7,016,717 B2 * | 3/2006 | Demos et al. ............... | 600/473 |

(Continued)

FOREIGN PATENT DOCUMENTS

EP 1 452 136 1/2004

(Continued)

OTHER PUBLICATIONS

Sackler Institute; Preliminary Synthesis of the First High Level Forum on Learning Sciences and Brain Research: Potential Implications for Education Policies and Practices: Brain Mechanisms and Early Learning; New York City, NY, USA, Jun. 16-17, 2000, pp. 1-28.

*Primary Examiner*—Eric Winakur
*Assistant Examiner*—Helene Bor

(57) ABSTRACT

A body activity measurement device is provided with a light irradiation unit that irradiates near infrared light of a specified wavelength on a specified measurement site of a brain of a subject; a light detector that detects the intensity of the light exiting from the measurement site; a light absorbance data generator that from the time sequence changes of the intensity of the exiting light generates light absorbance time sequence data suggesting the changes in the concentration of oxyHb, deoxyHb and totalHb; and multiple baseline correction units that correct baselines that mutually differ in relation to the light absorbance time sequence data obtained when the subject performs specified assignments; and configured such that the baseline correction of the light absorbance time sequence data can be conducted using the baseline correction units corresponding to the assignment performed by the subject.

17 Claims, 21 Drawing Sheets

U.S. PATENT DOCUMENTS

| | | | |
|---|---|---|---|
| 2002/0161290 A1* | 10/2002 | Chance | 600/323 |
| 2003/0187359 A1* | 10/2003 | Njemanze | 600/454 |
| 2004/0064052 A1* | 4/2004 | Chance et al. | 600/476 |
| 2004/0092809 A1* | 5/2004 | DeCharms | 600/410 |
| 2004/0236197 A1 | 11/2004 | Eda et al. | |
| 2006/0058683 A1* | 3/2006 | Chance | 600/476 |

FOREIGN PATENT DOCUMENTS

| | | |
|---|---|---|
| JP | 08-215179 | 8/1996 |
| JP | 09-098972 | 4/1997 |
| JP | 2000-237194 | 9/2000 |
| JP | 2002-177281 | 6/2002 |
| JP | 2002-107291 | 10/2002 |

* cited by examiner

BODY ACTIVITY MEASUREMENT DEVICE

FIELD OF THE INVENTION

The present invention relates to a body activity measurement device that uses light to measure body activity of a specified measurement site when a subject performs a specified assignment.

DESCRIPTION OF RELATED ART

Recent progress has been made in the development of body activity measurement devices that enable measurement of body activity without restraining the subject by utilizing light, specifically, near infrared light. Particular attention has been paid to the development of a device that can measure brain activity, which in the past was difficult to measure in an unrestrained state.

The realization of a non-invasive measurement of brain activity based on this kind of device has allowed scientific data indicating brain activity to be obtained when the subject performs a variety of assignments without having a severely restricted experimental environment. This kind of scientific data has been applied to a variety of fields. First of all, for example, it has been possible to acquire data indicating brain activity in a normal environment such as during study activities, and therefore, the brain function of subjects when performing specified training assignments have been measured and those results have been applied to education. Moreover, other applications have been made in the field of medicine, etc.

This type of device can comprise a light irradiation unit that irradiates near infrared light of a specified wavelength on the brain of a subject, a light detector that detects the intensity of the light exiting (light passing through and reflected light) from the aforementioned measurement site based on the irradiated light of this light irradiation unit, and a time sequence data generator that from the time sequence changes of the intensity of the exiting light that the light detector detects generated time sequence data indicating the time sequence changes of light absorbance at various wavelengths; and from the light absorbance values at the various wavelengths, the amount of change or the change in concentration can be calculated for oxygenated hemoglobin (oxyHb), deoxygenated hemoglobin (deoxyHb), and total hemoglobin (totalHb), which are bodily substances that participate in the hemodynamics (status of blood flow rate and/or amount of blood components) indicating brain activity.

In many of these devices, the time sequence data of the light absorbance is corrected by taking the initial time of performing an assignment as the measurement standard, and the amount of concentration of oxyHb, deoxyHb, and totalHb are derived at each time. In addition, included in the light absorbance time sequence data described above are the values of light absorbance changes based on factors that do not depend on the performance of the assignment, for example, the movement of the head, the basal metabolism of the brain such as brain noise, and drift. Therefore, some conventional devices are configured to provide a baseline correction unit that sets up a specified correction system, and generates data indicating the amount of change or the change of concentration in oxyHb, deoxyHb, and totalHb based on baseline corrected time sequence data. (Refer to Japanese Unexamined Patent Application Publication No. 2002-107291.)

However, in the past the approach to baseline correction was not particularly emphasized, and data was usually obtained only by setting up a measurement standard without implementing baseline correction, which is the data output from the device, or data corrected by a baseline correction unit provided in the device was used as is. Then, as described above, these data were used in research such as in medicine and education without further deliberation.

In this regard, data that diverge from values that are known by experience or that are theoretically possible may be obtained by this type of device depending on the assignment the subject performs.

Specifically, in academic research, for example, if an assignment given to a subject requires a high cognitive capacity, the hemodynamics caused by the psychological state of the subject such as being excited or tense may have a great influence on the data obtained. Meanwhile, in an assignment not requiring so much high cognitive capacity, it may be expected that the effect of the psychological state of the subject will not be that great. In addition, if the subject performs assignments configured such that a fixed period of rest is taken after the task, the hemodynamics during rest may also have a great influence on the data.

Nonetheless, in a conventional device, even if there were this kind of difference in the contents of the assignment or the performance conditions, a uniform baseline correction method was applied, or the baseline itself was not taken into consideration. Therefore, there remains room for doubt about the reliability of the data obtained.

Thus, the present inventors rethought the baseline correction system of time sequence data in conventional body activity measurement devices, and, focusing on the differences in baselines depending on the assignment performed by the subject, made exhaustive efforts to develop a body activity measurement device that reflects this difference in baselines, and that can obtain suitable data corresponding to the characteristics of the assignment.

The present invention intends to resolve the problems described above, and is a body activity measurement device comprising: a light irradiation unit that irradiates light of a specified wavelength on a specified measurement site of the body of a subject; a light detector that detects the intensity of the light exiting from the aforementioned measurement site based on the irradiated light of the light irradiation unit; a time sequence data generator that from the time sequence changes of the intensity of the exiting light that the light detector detects generates time sequence data suggesting the changes in amount or changes in concentration of a specified body substance participating in the body activity; and multiple baseline correction units that correct baselines that mutually differ in relation to the aforementioned time sequence data obtained when the aforementioned subject performs specified assignments; configured such that the aforementioned baseline correction of the time sequence data can be conducted using one or multiple baseline correction units corresponding to the assignment performed by the subject.

Further, here "assignment" means giving any kind of task such as a load, work or stimulus to induce bodily activity at a specified site in the body of the subject. For example, academic tests requiring cognitive capacity, psychological tests, and exercise, as well as other stimuli to the five senses such as vision and olfaction may be cited as concrete examples of tasks. In addition, if configured such that a time of intermission (rest) is taken before and after a task, this combination of task and rest shall be an "assignment".

Moreover, "corresponding to the assignment performed by the subject" means, for example, corresponding to the "content of the assignment", namely, the type of task used in the assignment, or the performance condition of the assignment; and, if the assignment is repeatedly conducted, this also means corresponding to the "cycles of the assignment", which are the times of performing the respective assignments. Further, this also means corresponding to the "type and frequency of the assignment" that, in terms of the experimental plan, are considered "accommodation" of the subject that can be produced by repeating the assignment.

Suitable concrete aspects of multiple baseline correction units include units that subtract the baseline data indicating the baseline from the time sequence data, and that produce new time sequence data; and the baseline data may be expressed as a function related to time in which the values of all or part of the time sequence data generated by the aforementioned time sequence data generator are used. The baseline units may be, for example, units that subtract the time sequence data obtained in an ordinary state in which the subject does not perform the assignment from the time sequence data obtained when performing the assignment. In this kind of unit the measurements are simple and the time sequence data and the baseline data can be obtained simultaneously by measuring only when performing the assignment. Moreover, by subtracting the baseline data that utilizes the value of the time sequence data obtained when the subject does not perform the assignment from the time sequence data obtained when performing the assignment, the baseline correction unit simultaneously sets up a photometer standard, a reference that appears in modified Lambert-Beer's law, thus it is not necessary to set up a separate photometer standard.

Then, the following will be cited as a concrete aspect of a multiple baseline correction unit suitable for realizing baseline correction corresponding to an assignment.

For example, when a subject repeatedly performs a specified assignment, it is preferable that the multiple baseline correction units comprise at least a baseline correction unit that expresses the baseline data by a function that references the values of the time sequence data at specified times during performance of the assignments. Baseline correction corresponding to cycles of a repeatedly performed assignment can be conducted by this kind of baseline correction unit.

Further, repeatedly performing a specified assignment not only comprises repeating an assignment that includes entirely the same task, but also comprises repeatedly performing an assignment that includes tasks that can be solved based on the same plan (method of solution). Moreover, if the "function that references the value of the time sequence data at a specified time during performance of the assignments" is a function that utilizes values of the time sequence data at one or multiple times obtained in the time in which the respective assignments are performed, functions may be set up for each assignment, or set up for each specified time of the assignment.

Specifically, if a repeated assignment comprises a task and a rest period in which the task is not given, concrete aspects of the baseline data may include: data expressed by a linear function set up for each task and each rest period, and determined by the values of the time sequence data at the initial times of the respective tasks and rest periods, and the values of the time sequence data at the final times; data expressed by a constant function that is set up for each task and each rest period, and that takes the values of the time sequence data at the initial time of the tasks and rest periods as the constant; and data expressed by a linear function set up between specified times of rest period, and determined by the values of the time sequence data at specified times of specified rest period, and the values of time sequence data at specified times of the following rest periods.

Meanwhile, if the subject is made to continuously perform assignments of differing content, preferably included in the multiple baseline correction units is at least a baseline correction unit that expresses the baseline data using a function that references the values of time sequence data at specified times during performances of the assignments. This kind of baseline correction unit can appropriately correct the baselines when set up such that the baselines differ because of differences in the contents of the assignments. Further, "continuously" not only means complete continuity, but also includes when performed at slight intervals.

More concretely, an example is baseline data expressed by constant functions that are set up for each assignment, and take the values of the time sequence data at the initial times of the assignments as the constant. Further, "set up for each assignment" means determined corresponding to the differences in the content of the assignments to be performed, and, if repeatedly performing an assignment of the same content, means determined in the interval from the initial time to the final time of repeated performance.

Moreover, in order to enable efficient measurements, a baseline correction unit extraction means is provided to extract from the aforementioned multiple baseline correction units the baseline correction units corresponding to the assignment the subject is made to perform. Preferably, the baseline correction units extracted by the extraction means conduct the baseline correction of the time sequence data. The baseline correction unit extraction means may extract the baseline correction units equivalent to the selection signals that the user inputs, or may automatically extract the baseline correction units corresponding to a task by information input relating to the assignment. Further, even if extracting only the unit judged optimum from the characteristics of the assignment, "to extract baseline correction units corresponding to an assignment" may include extracting all baseline correction units that use a multiple candidate baseline system determined to be applicable.

The effect of the invention can be particularly powerful if the device of the present invention is configured such that measurement sites are set up in the brain, and brain activity is measured as the body activity. Depending on the type of assignment the subject is made to perform, with brain activity it is possible that not only body-derived fluctuations and brain noise, but also the body signals induced by psychological states may have an extremely great influence on the time sequence data, and sometimes it may not be possible to set up a uniform baseline.

Assuming that a device utilizes light and measures activity inside the body, the light of a specified wavelength that is irradiated by the light irradiation unit is preferably light of the near infrared region. The reason is that light of the near infrared region passes through skin tissue and bone tissue.

The specified body substance participating in the body activity is preferably oxyHb and deoxyHb in the blood. The reason is that these oxyHb and deoxyHb are parameter substances that express changes in hemodynamics, which is one body activity; in addition, oxyHb and deoxyHb indicate the maximum absorbance in light of a specified wavelength in the near infrared and visible regions, and are thus suitable for optical measurement.

According to the body activity measurement device of the present invention, it is possible to selectively obtain from multiple baseline correction systems time sequence data with the optimum baseline correction corresponding to the assignment. Moreover, if a conventional device was used that could only obtain data wherein the baseline correction method adopted was applied as is, it is possible that new unnoticed data could be acquired, and thus new research discoveries in a variety of fields that use these data may be anticipated.

DETAILED DESCRIPTION OF THE PREFERRED EMBODIMENTS

A body activity measurement device 1 is one embodiment of the present invention, and will be explained using diagrams in the Figures.

Figure 1:
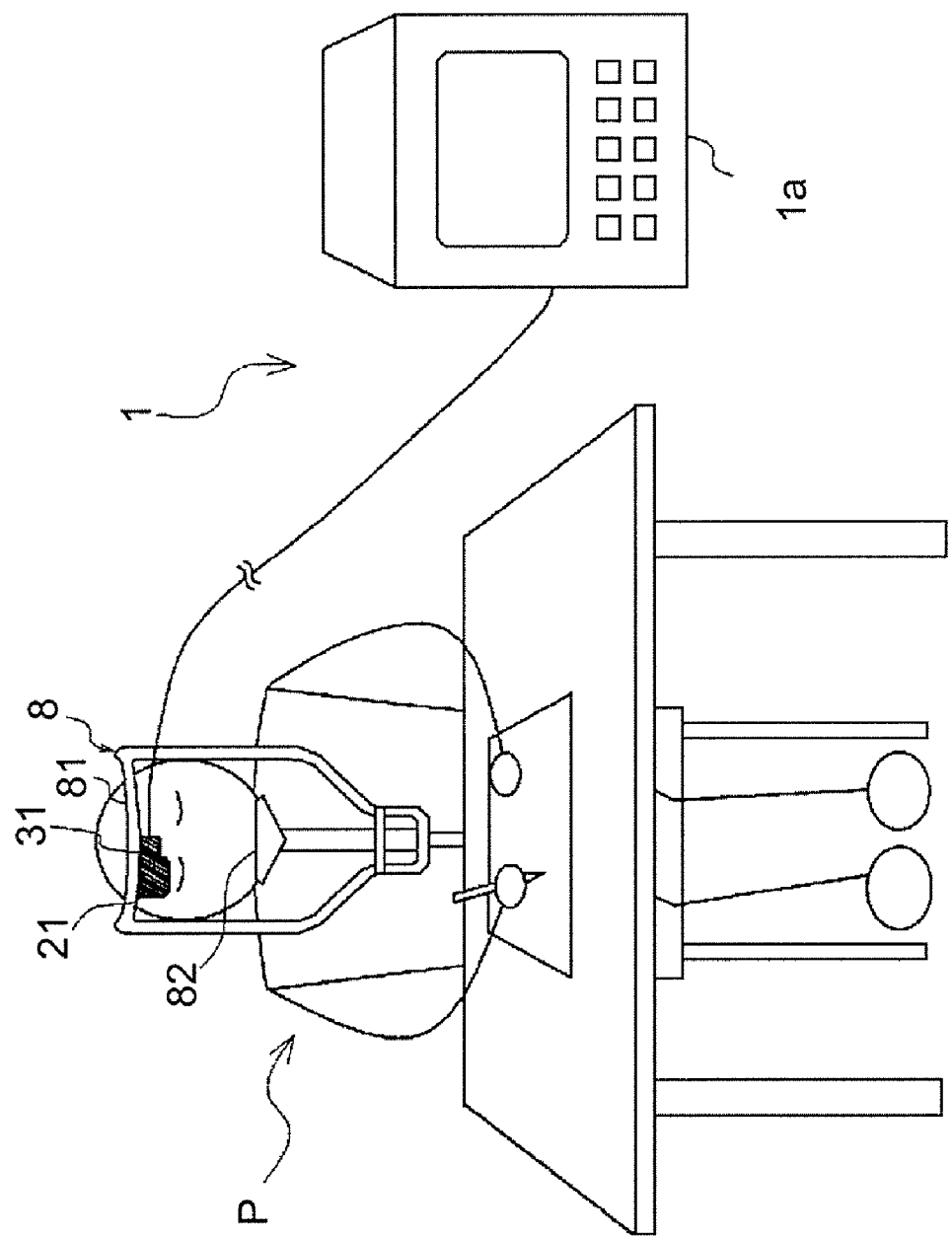
FIG. 1 is an overall schematic diagram indicating the body activity measurement device of one embodiment of the present invention.
Figure 3:
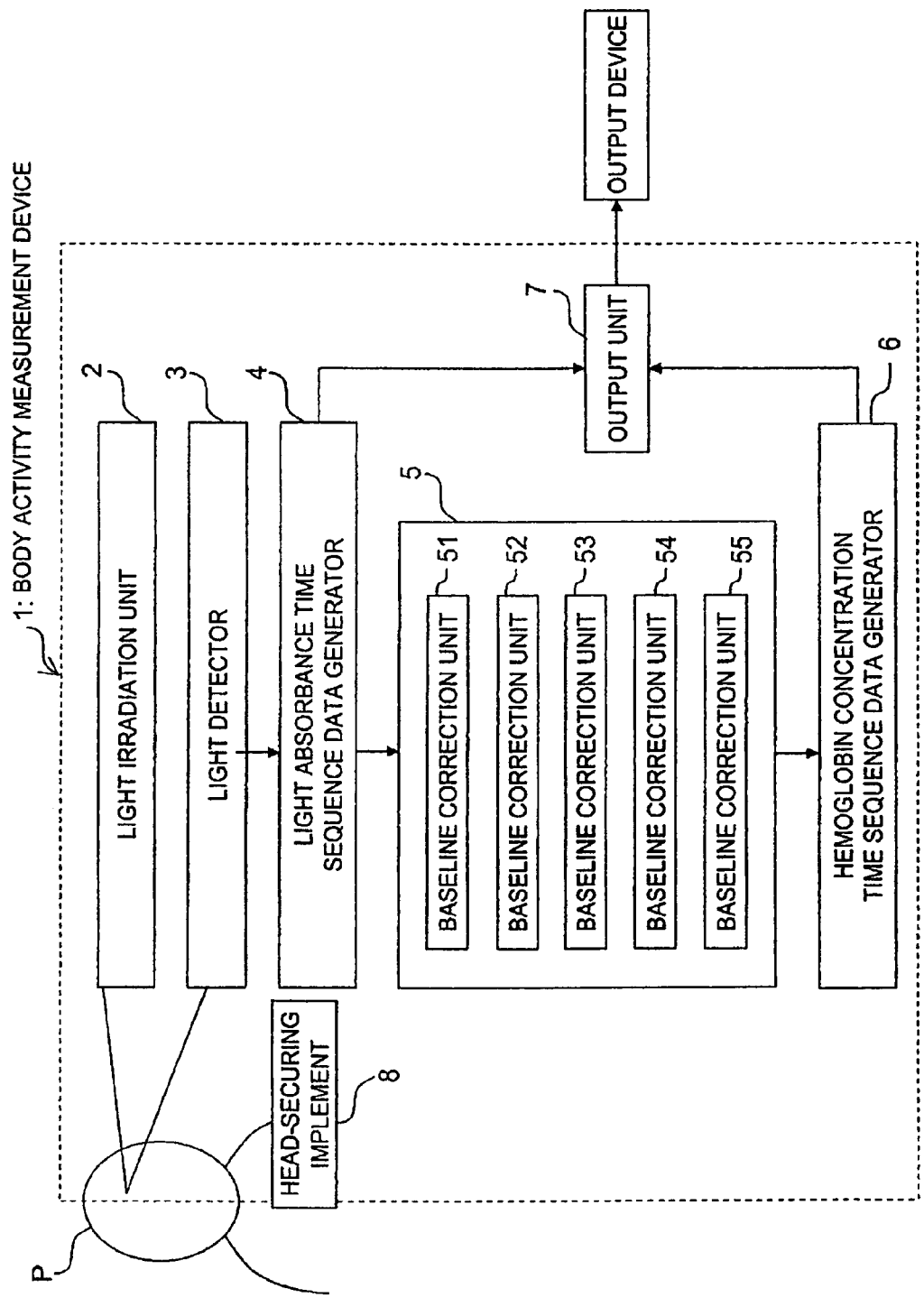
FIG. 3 is an overall function configurational diagram of the body activity measurement device of the same embodiment.

This body activity measurement device 1 utilizes NIRS (near infrared spectroscopy), and as indicated in FIGS. 1 and 3, is configured such that: near infrared light of a specified wavelength are irradiated on the head, which is the specified measurement site of the body of a subject P; the intensity of the light exiting the brain based on the irradiated light is detected time sequentially; light absorbance time sequence data, which is time sequence data suggesting the changes in relative concentrations of hemoglobin, the specified body substance participating in the body activity, are created from the time sequence changes of the intensity of the detected exiting light; and, from among mutually differing multiple baseline correction methods, it is possible to apply to the aforementioned light absorbance time sequence data to be obtained when the subject P is made to perform specified assignments, the baseline correction method corresponding to the assignment that the subject P is made to perform. Specifically, as an embodiment of the present invention, the body activity measurement device 1 is configured as the optimum device to measure the brain activity when the subject P is made to continuously perform multiple times two or more types of assignments with different contents and comprising a task and a rest period when the task is not given.

Specifically, the body activity measurement device 1 of the present embodiment comprises: a light irradiation unit 2; a light detector 3; a light absorbance time sequence data generator 4, which is a time sequence data generator; multiple baseline correction units 5; a hemoglobin concentration time sequence data generator 6; an output unit 7; and a head-securing implement 8.

The configuration of each part will be explained below.

Figure 2:
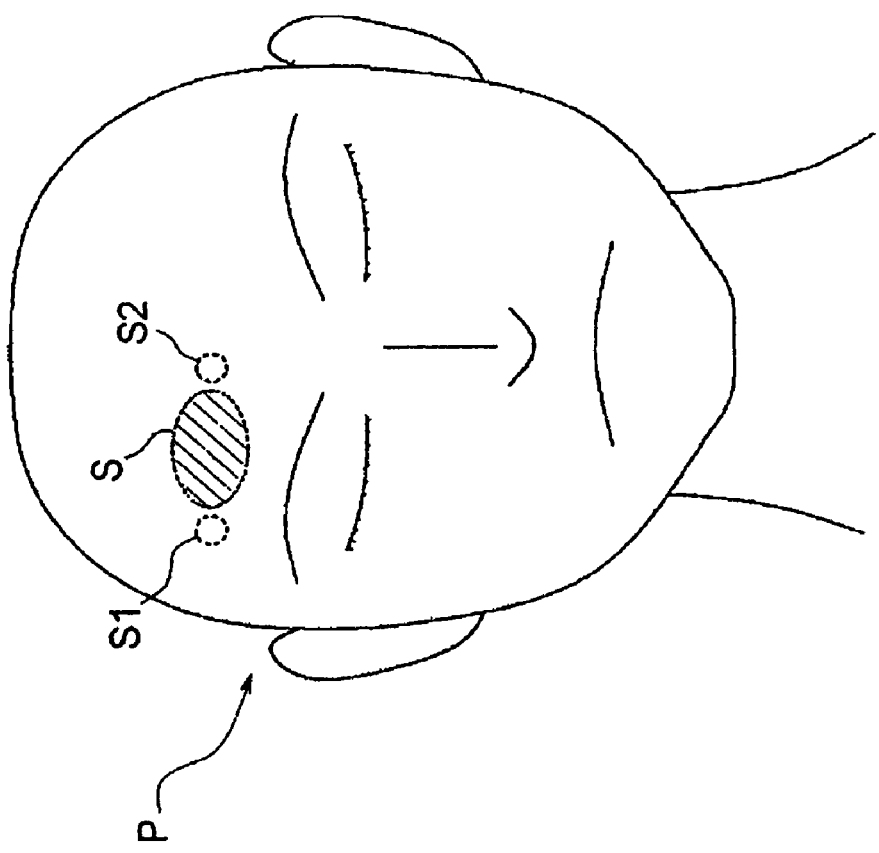
FIG. 2 is a partial explanatory diagram indicating the specified measurement site of the same embodiment.

The light irradiation unit 2 irradiates a specified site S (refer to FIG. 2) of the brain with near infrared light of multiple wavelengths (3 wavelengths in this embodiment) emitted from a semiconductor laser, or the like, as a light source. In the example indicated in the diagram, the light of the light source provided in the device main unit 1a is transmitted by optical fibers such that the light is irradiated on the brain by a light incidence unit 21 (refer to FIG. 1).

The light detector 3 receives the aforementioned near infrared light, which are the light irradiated by the aforementioned light irradiation unit 2 reflected from the brain, by light receiving elements such as photomultiplier tubes or CCD elements, and the intensity thereof is converted to electronic signals. In the example indicated in the diagrams, the light reflected from the brain is collected by a light collector 31 (refer to FIG. 1), and the light is transmitted to the light receiving elements by optical fibers.

The present embodiment uses a one-channel device providing the aforementioned light incidence unit 21 and the light collector 31 as a pair, and the light incidence unit 21 and light collector 31 are respectively mounted at specified regions S1 and S2 of the forehead of the subject P in order to measure the dynamics of the bodily substances oxyHb (hemoglobin oxide) and deoxyHb (hemoglobin) at the single specified measurement site S of the brain between them. Here, the measurement site S is set up, for example, in the frontal lobe of the brain, but first a brain structure image of the subject P was obtained using a brain structure measurement device such as an MRI (Magnetic Resonance Imaging)

which subjects the brain tissue to both electromagnetic radiation and a magnetic field to provide a composite image, and the site S was specified based on the image. Further, the measurement site may be varied depending on the content of the assignment.

The light absorbance time sequence data generator 4 generates light absorbance time sequence data, which are the data that indicate the changes of light absorbance over time by: acquiring sequentially over time and sampling at specified intervals the intensity signals of the exiting light of the various wavelengths that the detector 2 detects in the process of the subject P performing the assignment; converting these intensity signals logarithmically and calculating the light absorbance of the various wavelengths; relating the absorbance thereof with a time axis; and storing the data in a specified memory unit. In this embodiment a CPU is used for digital processing, but, of course, the absorbance time sequence data may also be generated by analog processing.

The multiple baseline correction units 5 correct the baseline in relation to the absorbance time sequence data generated by the aforementioned light absorbance time sequence data generator 4. Then, the present embodiment is configured such that the computations by which all of the multiple baseline correction units make baseline corrections to the light absorbance time sequence data are implemented by inputting baseline correction command signals. In addition, the device may also be set up so that baseline correction is automatically conducted after the aforementioned light absorbance time sequence data is displayed. These multiple baseline correction units 5 are configured such that corrections are made by subtracting the baseline data indicating the baseline from the absorbance time sequence data, and these baseline data are expressed by functions related to time referencing the values of part of the absorbance time sequence data generated (values at specified times). In the present embodiment, at least the following five baseline correction units 51, 52, 53, 54, and 55 are provided.

In order to enable application when repeatedly performing an assignment comprising a specified task and a rest period when that task is not given, the baseline correction units 51, 52, and 53 are configured such that the light absorbance time sequence data are corrected using baseline data expressed by functions referencing the values of light absorbance time sequence data at specified times during repeated assignment performance.

Figure 7:
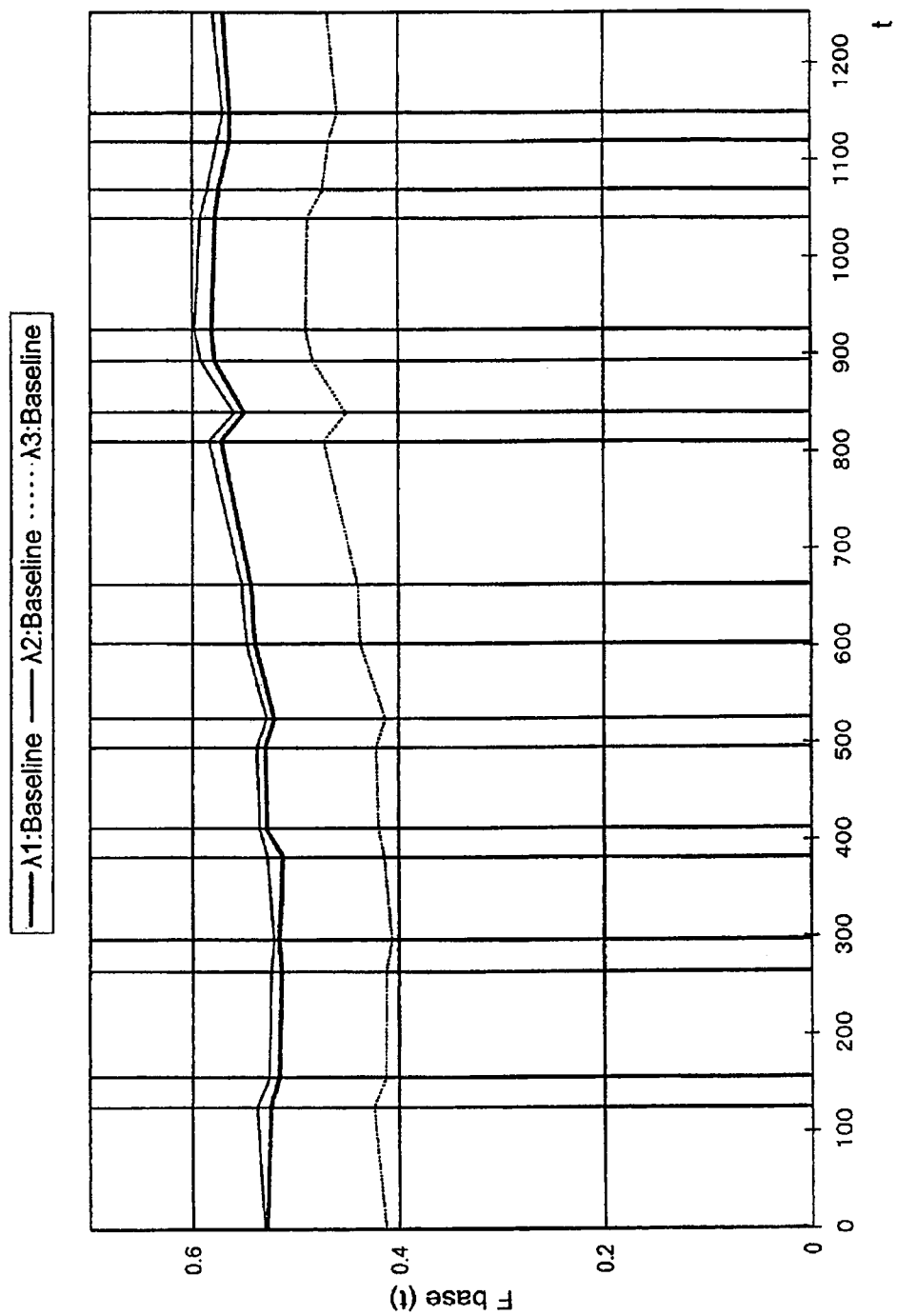
FIG. 7 is a graph indicating the baseline in the same embodiment.
Figure 8:
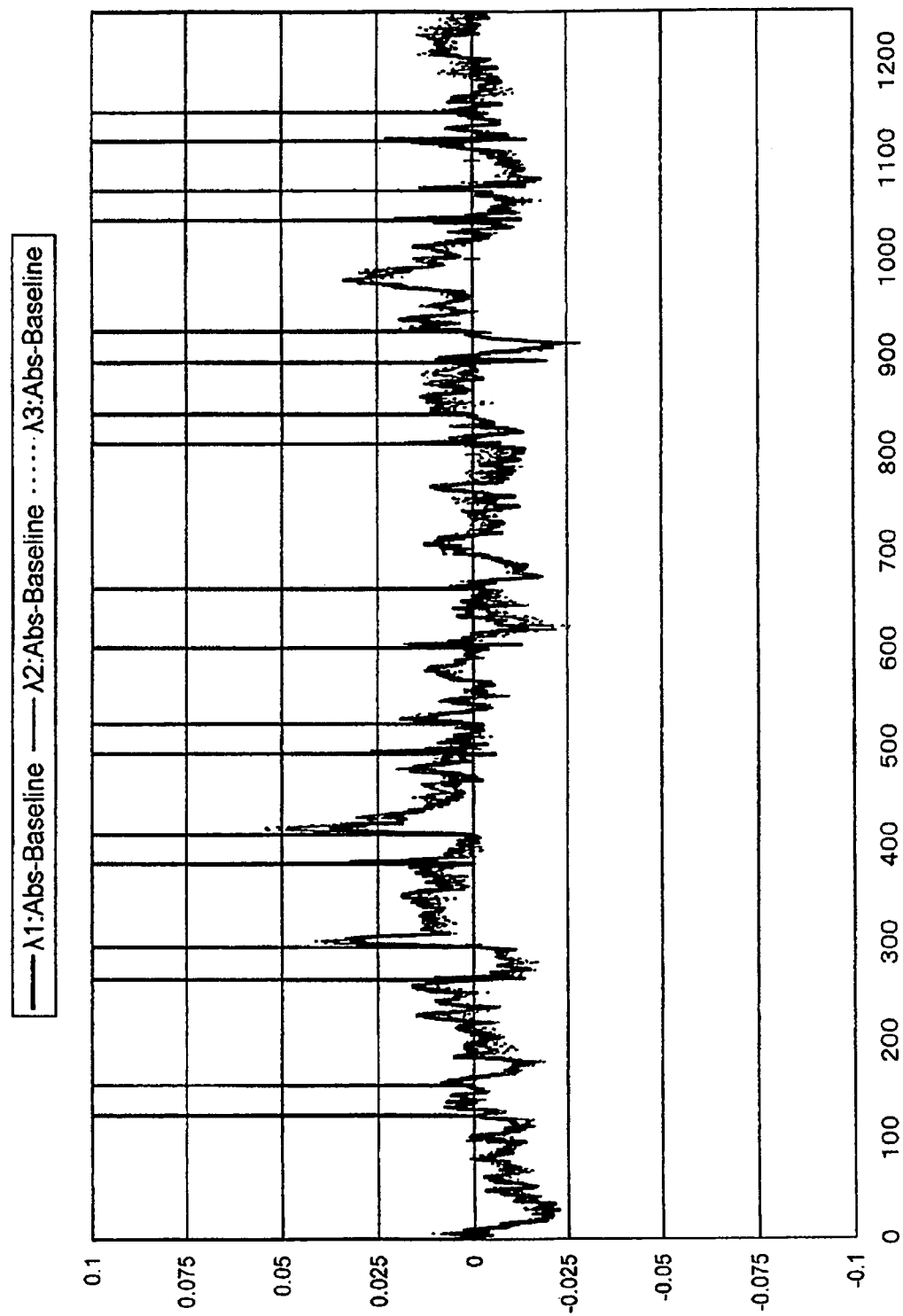
FIG. 8 is a waveform diagram indicating light absorption time sequence data corrected by a baseline correction unit of the same embodiment.
Figure 9:
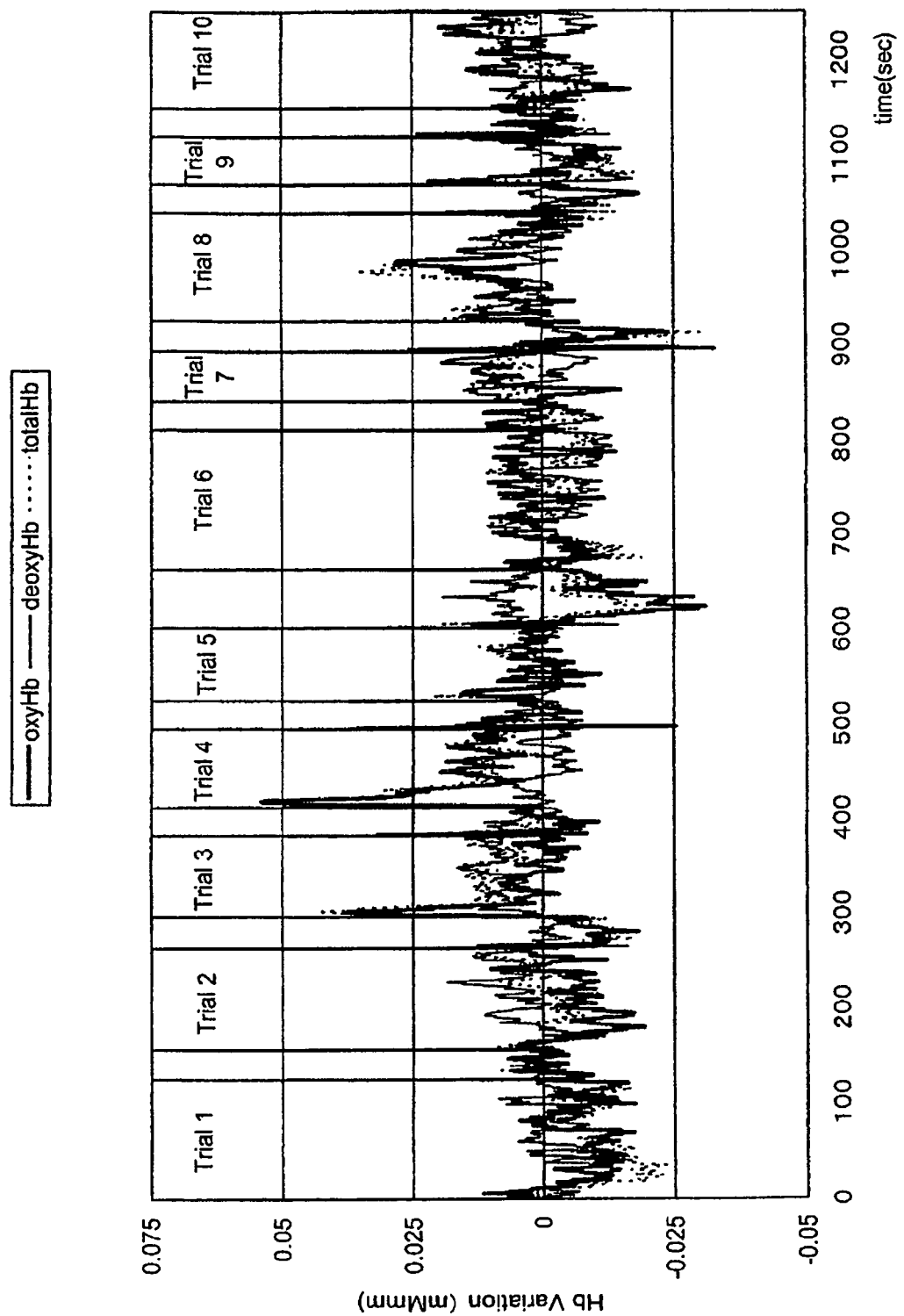
FIG. 9 is a waveform diagram indicating changes in the hemoglobin concentration time sequence data in the same embodiment.
Figure 10:
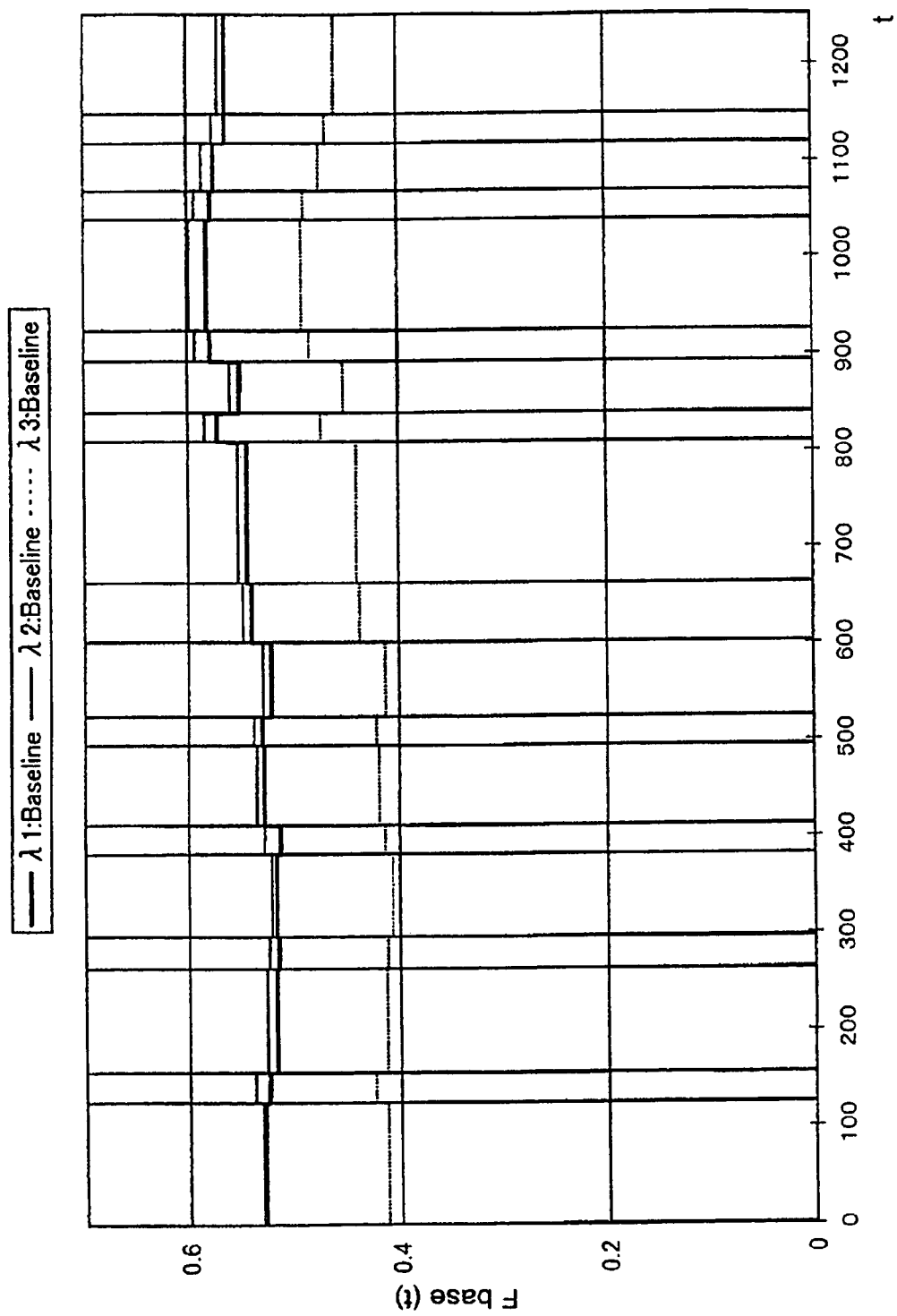
FIG. 10 is a graph indicating the baseline in the same embodiment.
Figure 11:
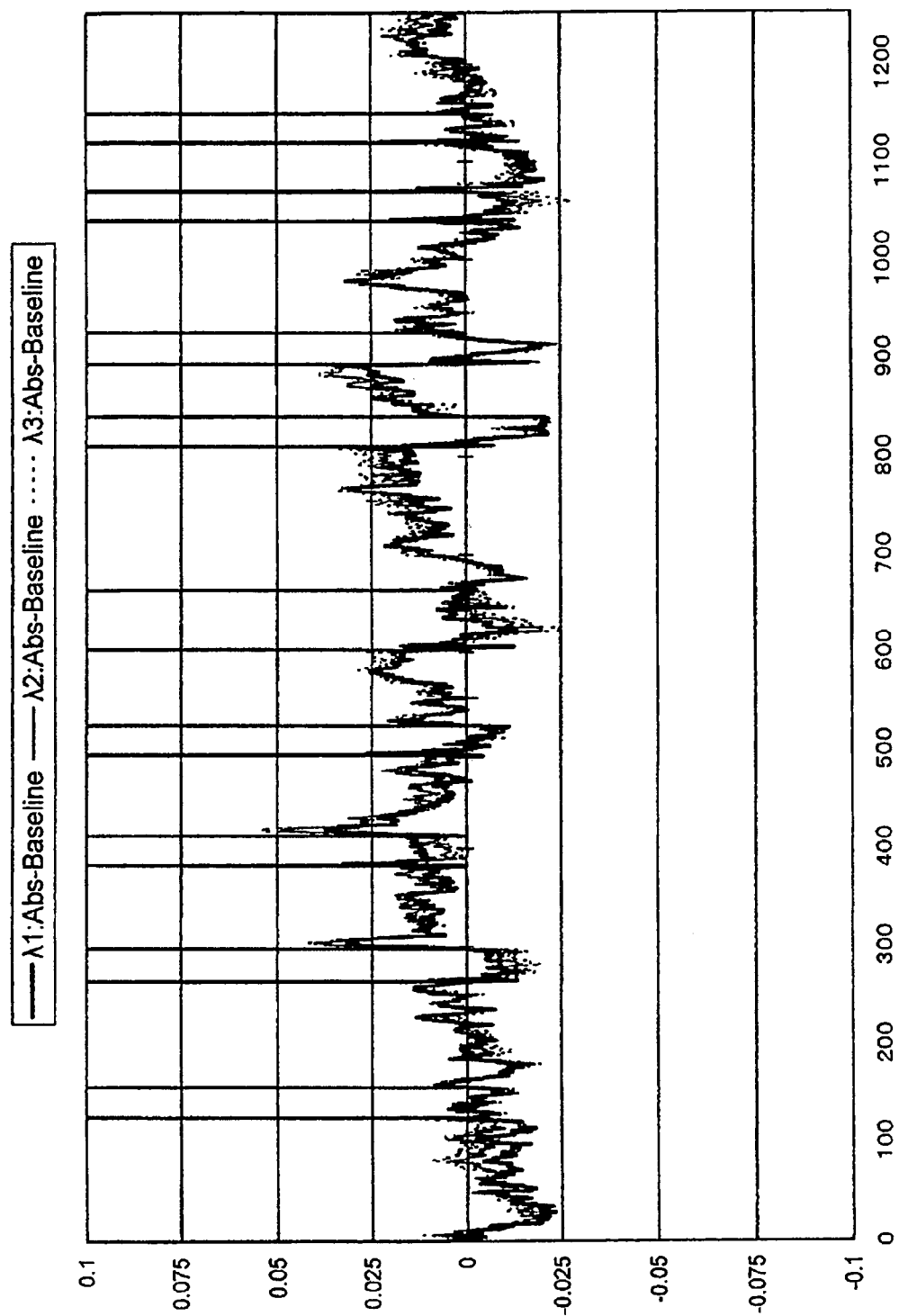
FIG. 11 is a waveform diagram indicating light absorption time sequence data corrected by a baseline correction unit of the same embodiment.
Figure 12:
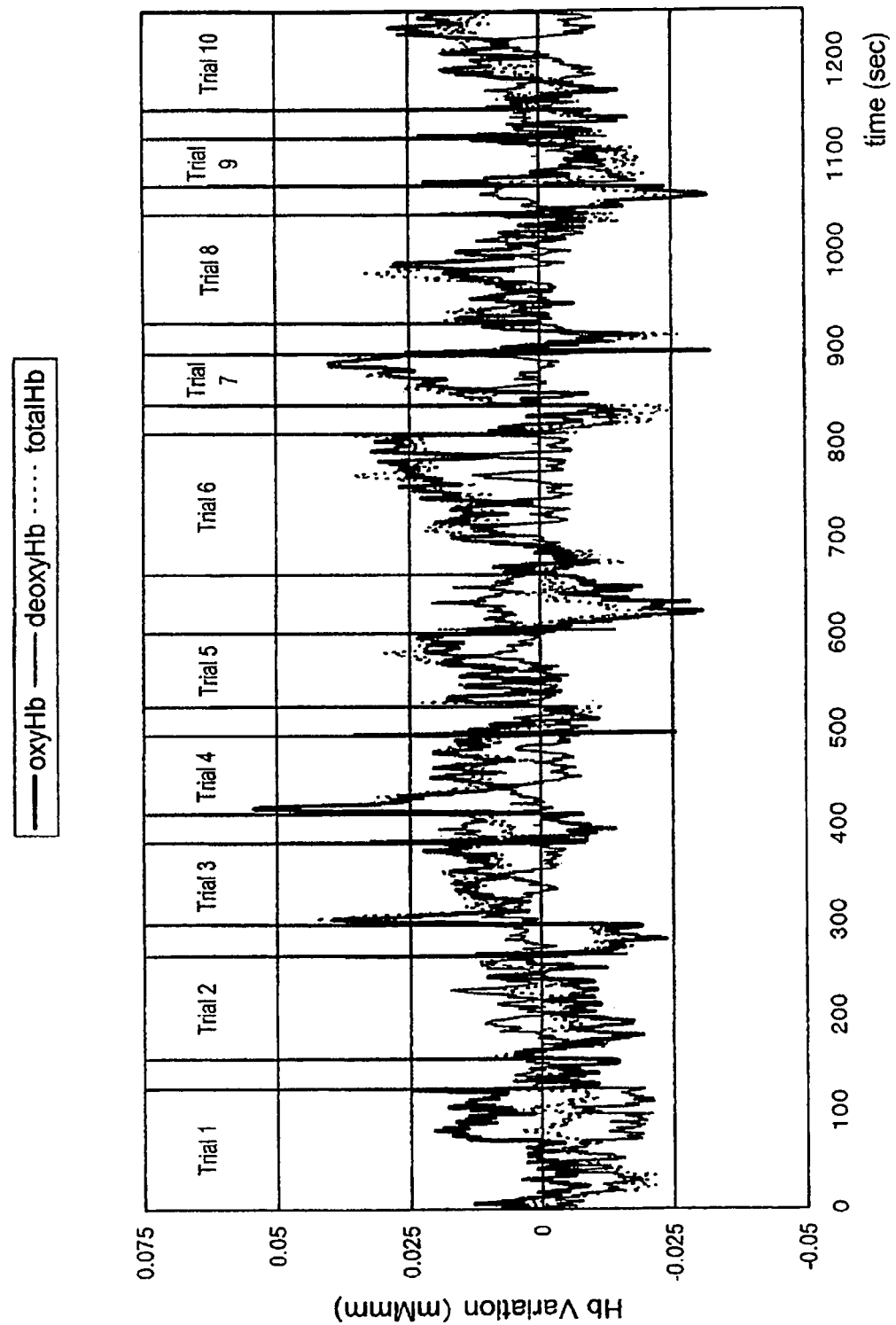
FIG. 12 is a waveform diagram indicating changes in the hemoglobin concentration time sequence data in the same embodiment.
Figure 13:
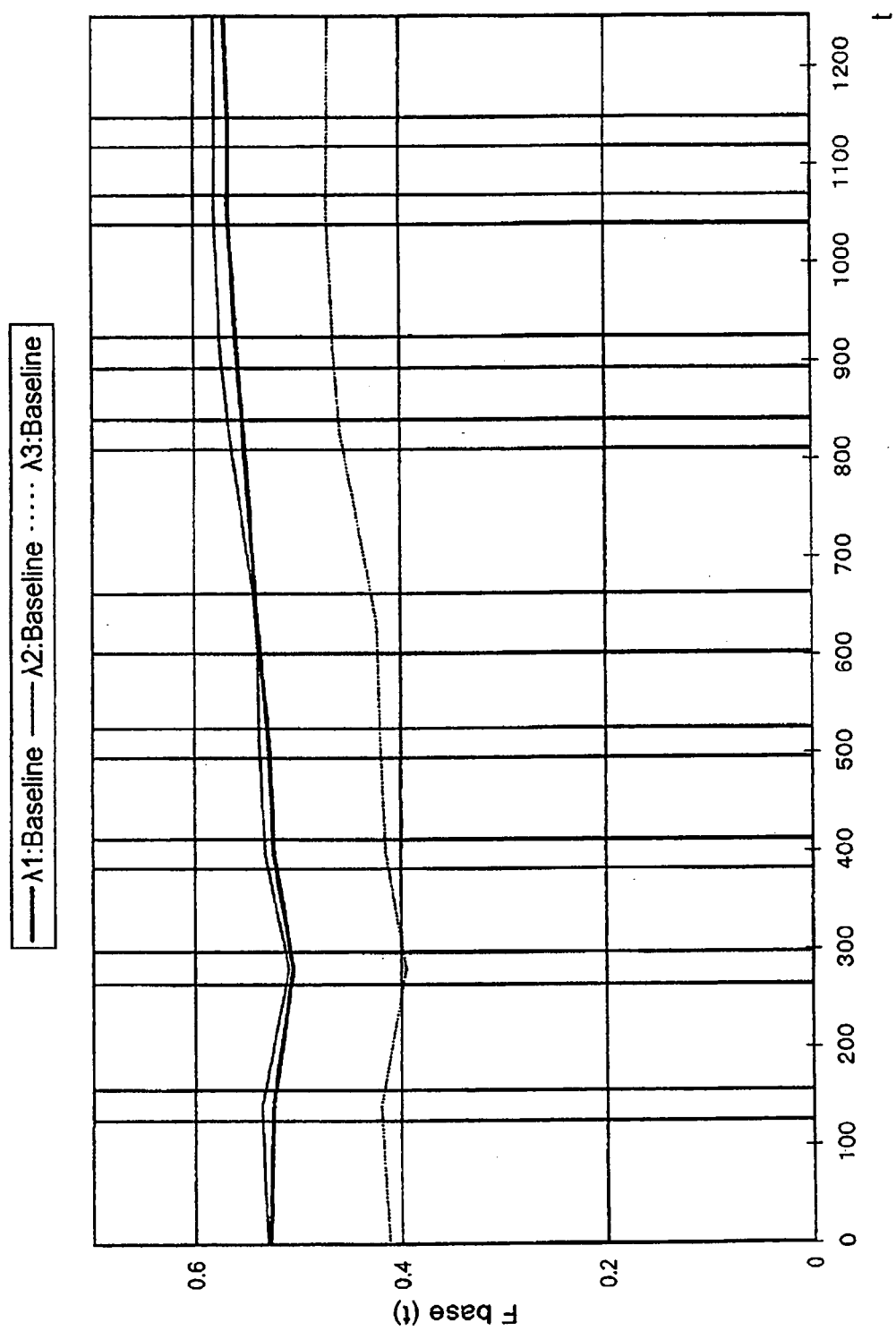
FIG. 13 is a graph indicating the baseline in the same embodiment.
Figure 14:
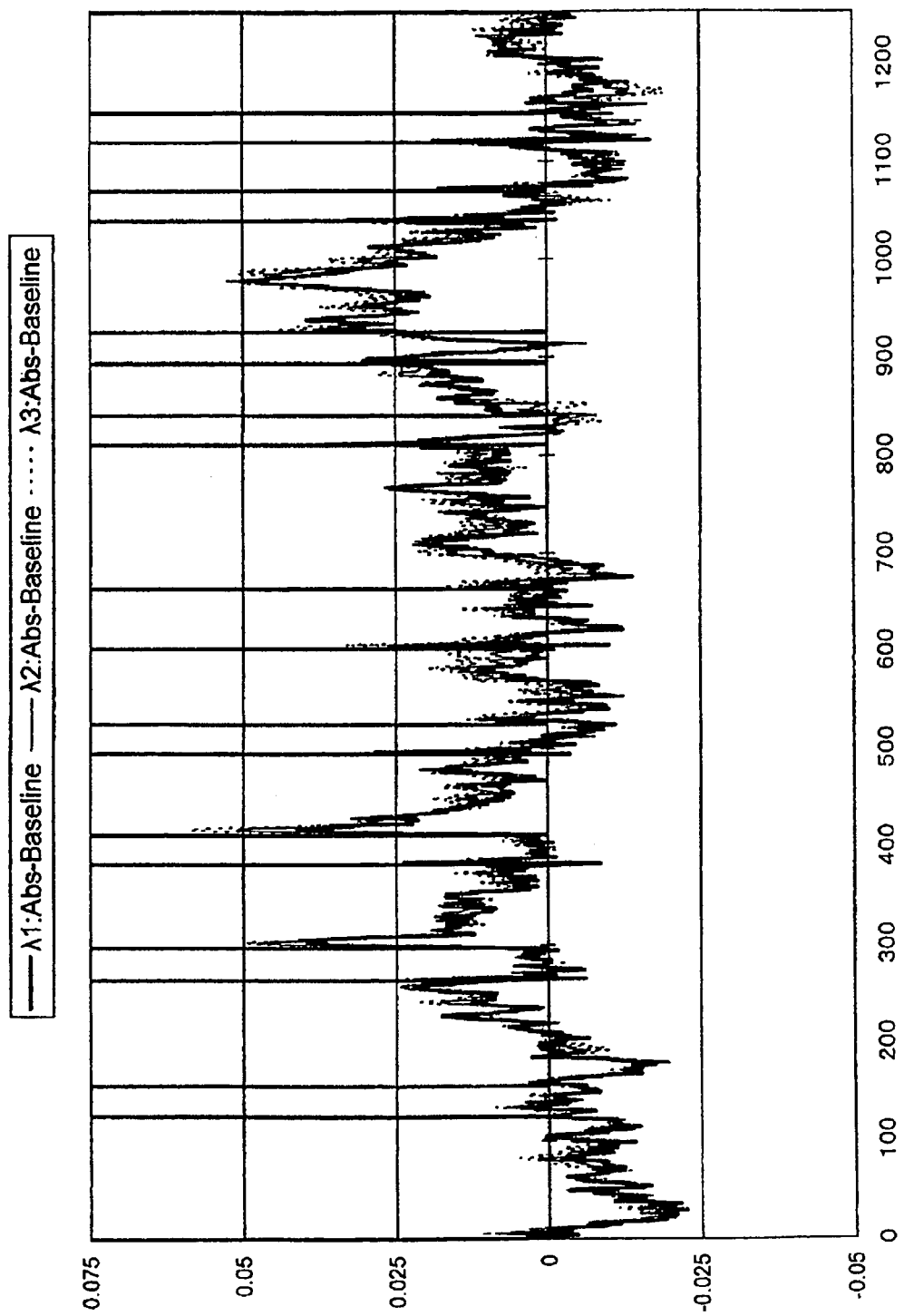
FIG. 14 is a waveform diagram indicating light absorption time sequence data corrected by a baseline correction unit of the same embodiment.
Figure 15:
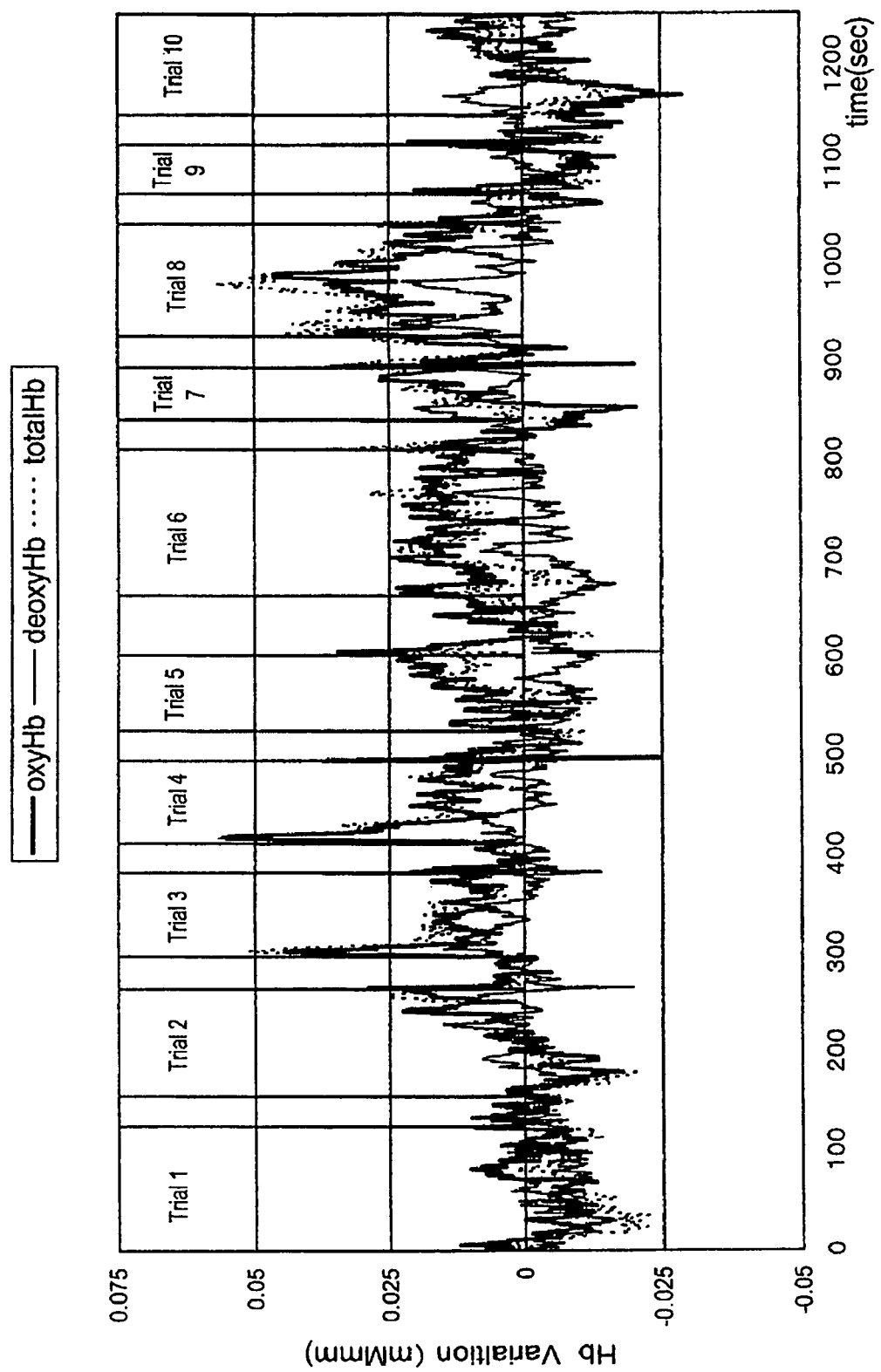
FIG. 15 is a waveform diagram indicating changes in the hemoglobin concentration time sequence data in the same embodiment.
Figure 16:
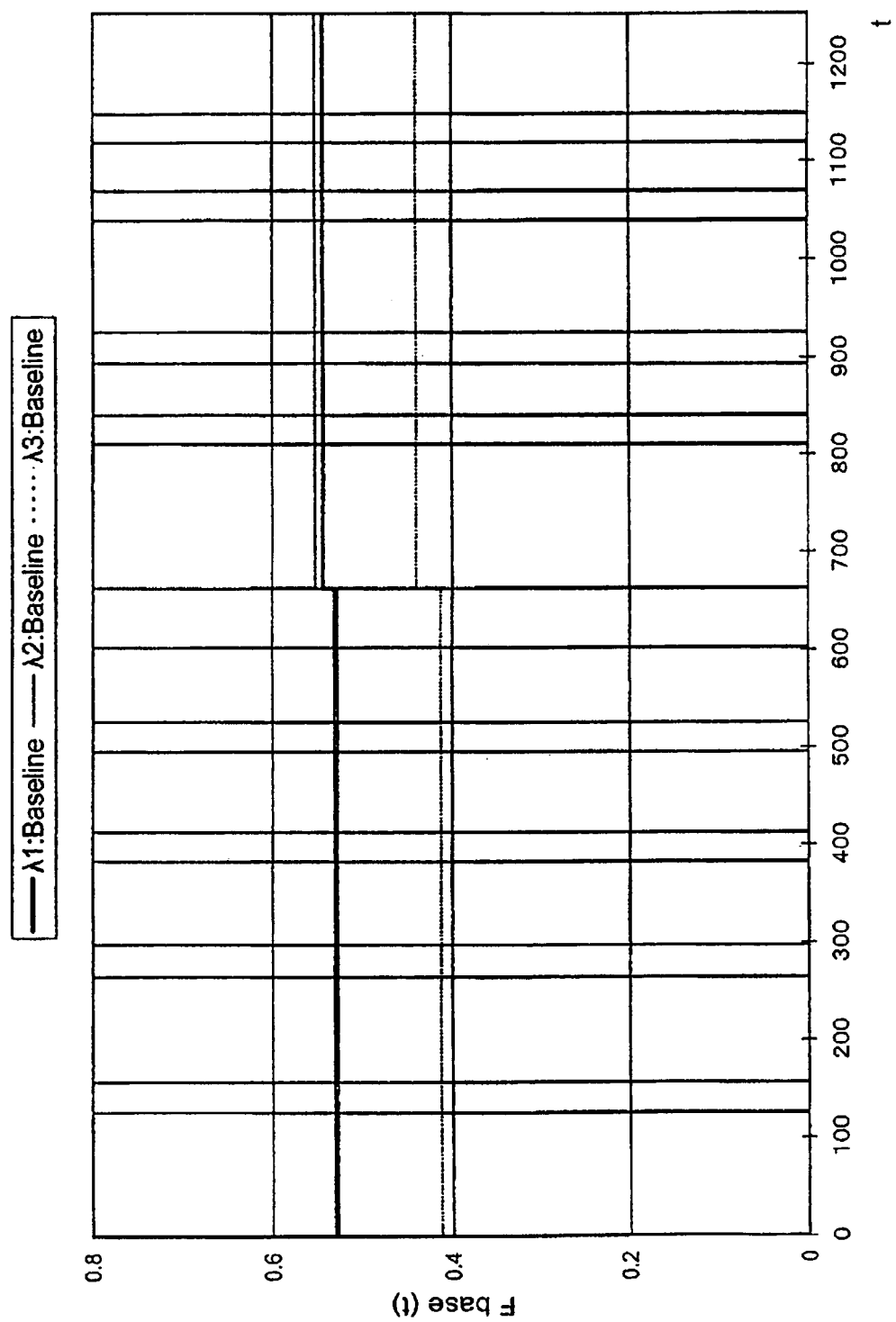
FIG. 16 is a graph indicating the baseline in the same embodiment.
Figure 17:
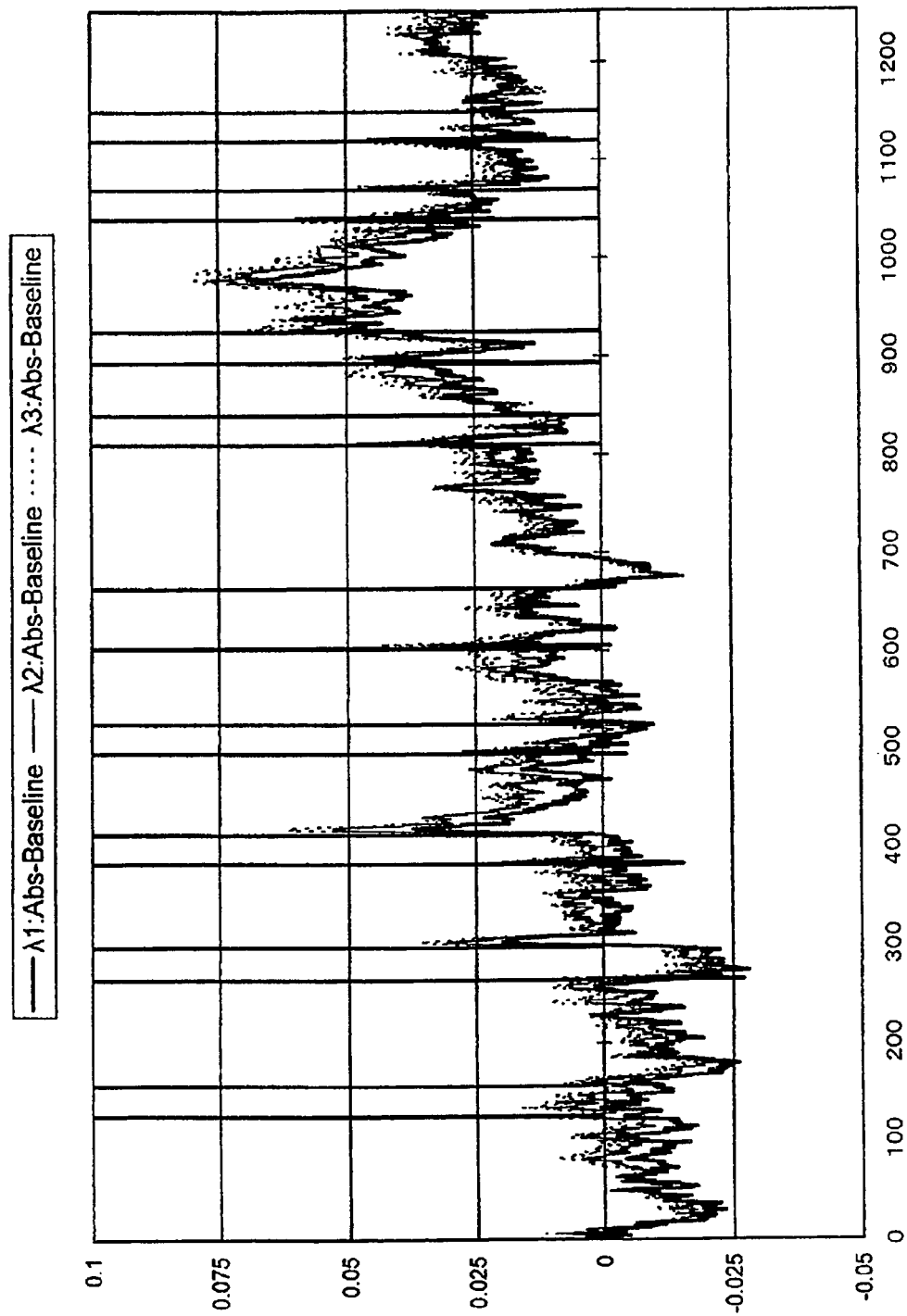
FIG. 17 is a waveform diagram indicating light absorption time sequence data corrected by a baseline correction unit of the same embodiment.
Figure 18:
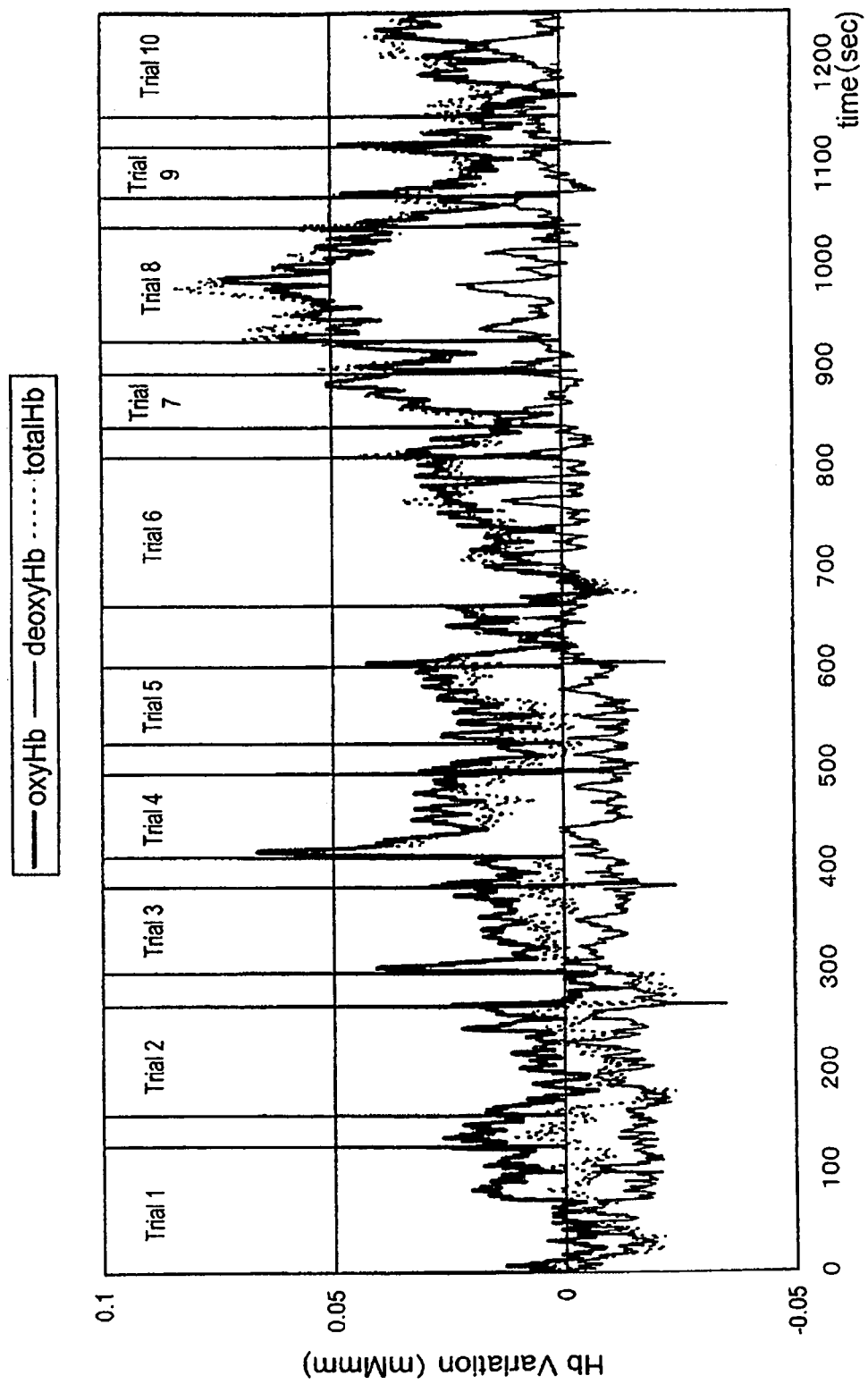
FIG. 18 is a waveform diagram indicating changes in the hemoglobin concentration time sequence data in the same embodiment.

Specifically, the baseline correction unit 51 corrects the light absorbance time sequence data based on baseline data (refer to FIG. 7) expressed by a linear function set up for each task and rest period, and determined by the respective task and rest period light absorbance time sequence data values at the initial times, and light absorbance time sequence data values at the final times. That is, if we let $A_{TASKn}1$ ($A_{RESTn}1$) be the value of the light absorbance of the initial time $T_{TASKn}1$ ($T_{RESTn}1$) of the specified task and rest period, and we let $A_{TASKn}2$ ($A_{RESTn}2$) be the value of the light absorbance of the final time $T_{TASKn}2$ ($T_{RESTn}2$), then the function $F_{base}$ (t) of time t indicating the baseline data used by this baseline correction unit 51 is expressed by:

at $T_{TASKn}1 \leq t \leq T_{TASKn}2$ $F_{base}(t)=(A_{TASKn}2-A_{TASKn}1)/(T_{TASKn}2-T_{TASKn}1)\times(t-T_{TASKn}1)+A_{TASKn}1$ at $T_{RESTn}1 \leq t \leq T_{RESTn}2$ $F_{base}(t)=(A_{RESTn}2-A_{RESTn}1)/(T_{RESTn}2-T_{RESTn}1)\times(t-T_{RESTn}1)+A_{RESTn}1$ The baseline correction unit 52 corrects the light absorbance time sequence data based on baseline data (refer to FIG. 10) expressed by a constant function that is set up for each task and rest period, and that takes as the constant the respective task and rest period light absorbance time sequence data values at the initial times. That is, if we let $A_{TASKn}1$ ($A_{RESTn}1$) be the value of the light absorbance of the initial time $T_{TASKn}1$ ($T_{RESTn}1$) of the specified task and rest period, and we let $A_{TASKn}2$ ($A_{RESTn}2$) be the value of the light absorbance of the final time $T_{TASKn}2$ ($T_{RESTn}2$), then the function $F_{base}$ (t) of time t indicating the baseline data used by this baseline correction unit 52 is expressed by:

at $T_{TASKn}1 \leq t \leq T_{TASKn}2$ $F_{base}(t)=A_{TASKn}1$ at $T_{RESTn}1 \leq t \leq T_{RESTn}2$ $F_{base}(t)=A_{RESTn}1$ The baseline correction unit 53 corrects the light absorbance time sequence data based on baseline data (refer to FIG. 13) expressed by a linear function set up for each interval of rest period intermediate times, and determined by the absorbance time sequence data values at the specified intermediate times of rest periods, and the light absorbance time sequence data values following the intermediate time periods of rest. If we let $A_{REST\ PERIODn}3$ be the value of the light absorbance of the intermediate time $T_{RESTn}3$ of the specified rest period, and we let $A_{RESTn+1}3$ be the value of the light absorbance of the intermediate time $T_{RESTn+1}3$ of the next rest period, then the function $F_{base}$ (t) of time t indicating the baseline data used by this baseline correction unit 53 is expressed by:

at $T_{RESTn}3 \leq t \leq T_{RESTn+1}3$ $F_{base}(t)=(A_{RESTn+1}3-A_{RESTn}3)/(T_{RESTn+1}3-T_{RESTn}3)\times(t-T_{RESTn}3)+A_{RESTn}3$ Moreover, the baseline correction unit 54 can be used when continuously performing two or more types of assignments with different content, and can correct light absorbance time sequence data based on baseline data expressed by a function referencing the values of light absorbance time sequence data at specified times during assignment performance. More concretely, the aforementioned baseline data is expressed by a constant function that is set up for each assignment, and that takes as the constant the respective light absorbance time sequence data values at the initial times of the assignments. The present embodiment is configured such that, after repeating the assignments of specified contents, a correspondence can be made to when the assignments of differing contents are repeated; specifically, if we let $A_{TERMn}1$ be the value of the light absorbance of the initial time $T_{TERMn}1$ of period in which the same assignment is repeated, and we let $A_{TERMn}2$ be the value of the light absorbance of the final time $T_{TERMn}2$, then the function $F_{base}(t)$ of time t indicating the baseline data used by this baseline correction unit 54 is expressed by:

at $T_{TERMn}1 \leq t \leq T_{TERMn}2$ $F_{base}(t)=A_{TERMn}1$

Figure 19:
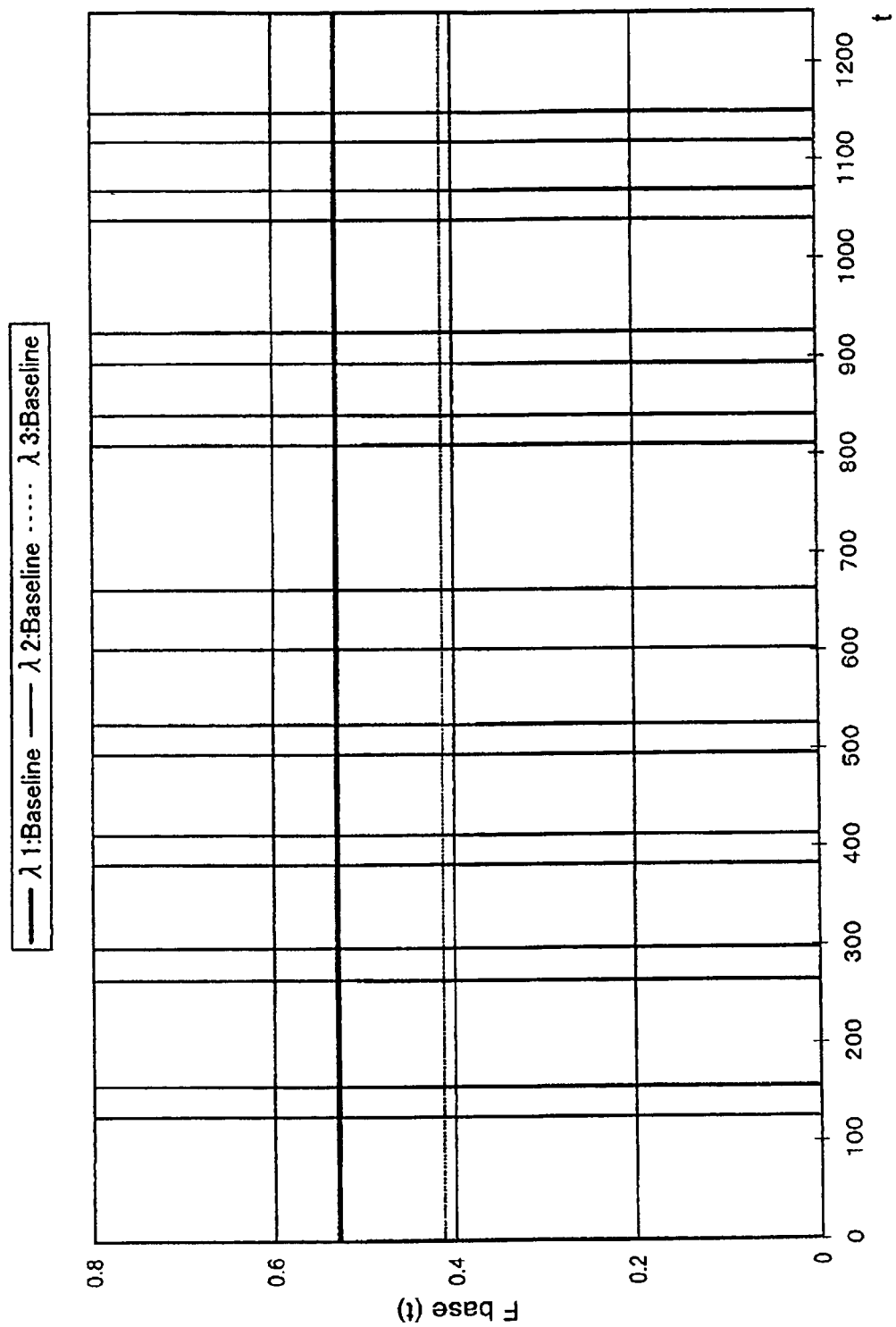
FIG. 19 is a graph indicating the baseline in the same embodiment.

The baseline correction unit 55 corrects the baseline based on baseline data (refer to FIG. 19) expressed by a constant function that takes as the constant the value of the light absorbance time sequence data at the initial time of performing the assignment, and only the conventional optical measurement standards are set up by adopting the correction method in which the light absorbance of the initial time is taken to be zero.

The hemoglobin concentration time sequence data generator 6 calculates the changes of oxyHb concentration, deoxyhb concentration and totalHb concentration derived from the oxyHb concentration and the deoxyHb concentration based on using the Modified Lambert-Beer Law to compute and process the values of the light absorbance time sequence data of 3 wavelengths corrected by the baseline correction units 5. These values are related with a corresponding time axis and stored in a specified memory unit, thus generating hemoglobin concentration time sequence data indicating the relative concentration changes of the oxyHb, deoxyHb and totalHb respectively along the time axis.

Figure 6:
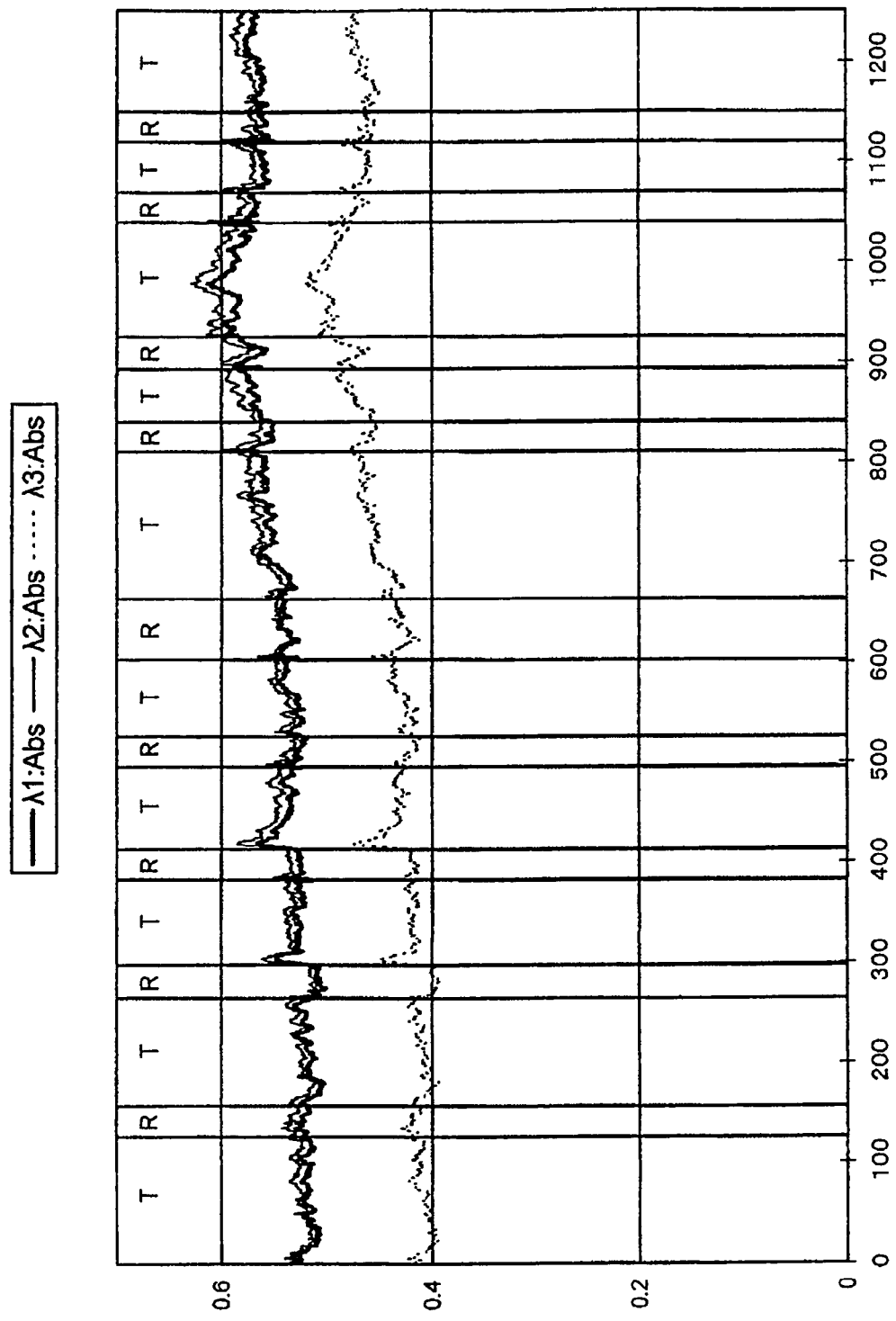
FIG. 6 is a waveform diagram indicating light absorption time sequence data obtained during performance of an assignment of the same embodiment.

At a minimum, the output unit 7 outputs to an output device such as a display or a printer the baseline data adopted by the baseline correction units 51 to 55, the absorbance time sequence data corrected by the baseline data and the aforementioned hemoglobin concentration time sequence data. In addition, as indicated in FIGS. 7, 10, 13, 16 and 19, the aforementioned corrected light absorption time sequence data are output as waveforms, and in FIGS. 9, 12, 15, 18 and 21, the hemoglobin concentration time sequence data are output as waveforms. Further, in the present embodiment, the initial times and final times of the tasks and the initial times and final times of the rest periods in the process of the subject P performing the assignments are simultaneously output following the time sequence as graphs indicating the baseline data, as waveforms of the corrected light absorbance time sequence data, and as waveforms of the hemoglobin concentration time sequence data. As long as the initial and final timings of the tasks and the initial and final timings of the rest periods can be compared as graphs indicating the baseline data, as waveforms of the corrected light absorbance time sequence data, or as waveforms of the hemoglobin concentration time sequence data, the output may be in any form. As in the examples in the diagrams, output in the figure of intersecting line segments is easy to understand. Further, as represented by the waveforms of the raw light absorbance time sequence data indicated in FIG. 6, the parts expressing the tasks and rest periods are indicated by T and R respectively. In the present embodiment the initial and final timings of the tasks and rest periods are measured using photography, for example, videos, but means that can automatically identify these timings may also be provided.

As indicated in FIG. 1, an example of the head-securing implement 8 may comprise a forehead support part 81 to support the upper part of the forehead, a jaw support part 82 to support the jaw of the subject P, and a securing part not indicated in the diagram for securing the forehead support part 81 and the jaw support part 82 so as not to move in relation to the desk or floor where the subject P is seated. As much as possible, this head-securing implement 8 suppresses movement of the head in order to obtain reliable data.

If measuring brain activity when the subject P is performing an assignment using the body activity measurement device 1 configured in the manner above, as indicated in FIG. 1, the light incidence unit 21 and the light collector 31 are mounted on the forehead of the subject P, and the measurements are taken while performing the assignments with the movement of the head restrained by the head-securing implement 8.

Embodiment 1 and embodiment 2, in which the brain activity was measured while the subject P performed specified assignments, will be explained below using the body activity measurement device 1 of the present embodiment.

EMBODIMENT 1

First, the assignments that the subject P performed will be explained. Here, the subject P was made to continuously perform assignments K1 and K2 indicated in FIGS. 4 and 5 respectively, and the first assignment K1 was repeatedly performed 5 times, and then the assignment K2 was repeatedly performed 5 times. Both assignments K1 and K2 comprised tasks and rest periods taken after performing the tasks during which the tasks were not performed.

Figure 4:
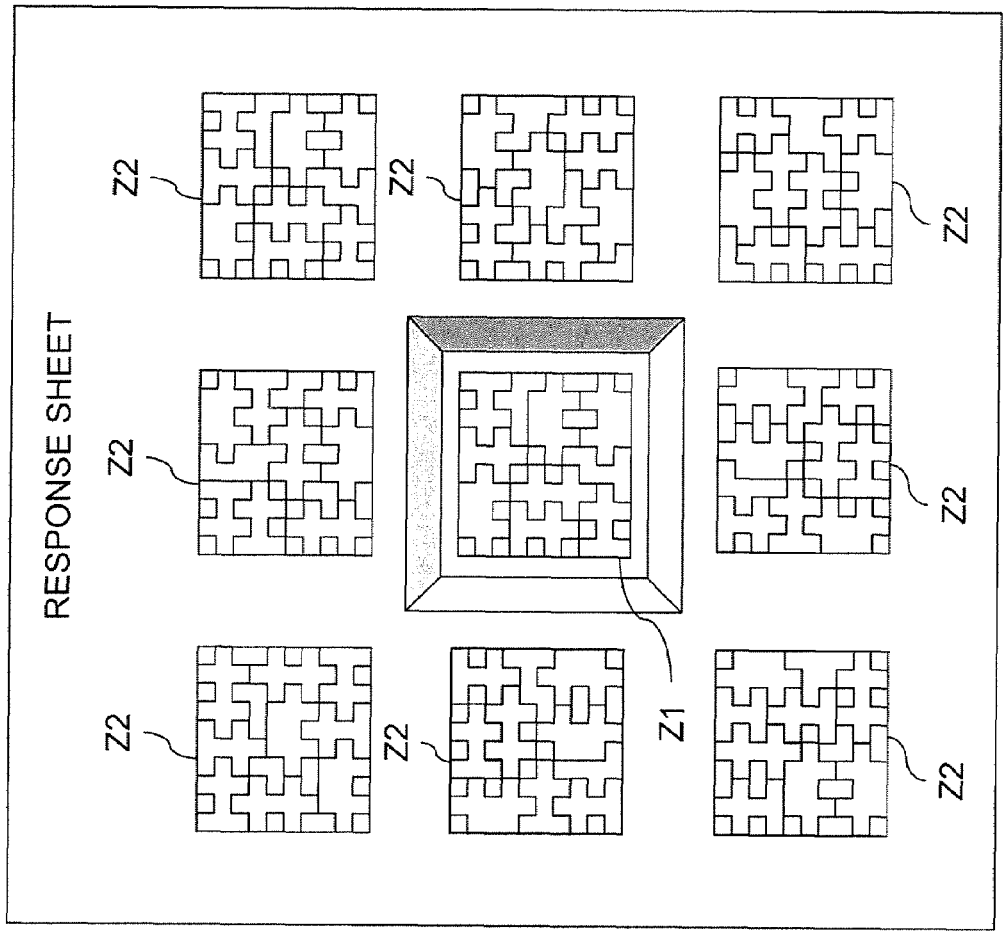
FIG. 4 is a diagram indicating the contents of assignment K1 of the same embodiment.
Figure 4:
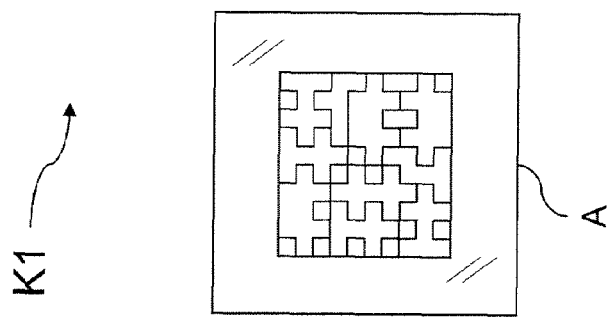

The task given in the assignment K1 is to solve how many of the given multiple assignment figures Z2 match with the two dimensional designated figure Z1 for which a specified pattern is depicted as in FIG. 4, and to determine whether or not there is the match described above by using a transparent supplement sheet A on which patterns are printed that match with the aforementioned designated figure Z1. Further, it is set up so that parallel, symmetric and rotated patterns also match with the indicated form Z1. The example in the diagram depicts a pattern that combines multiple lines in a square (for example, 3.2 cm×3.2 cm) arranged in the center of the response sheet. Moreover, the assignment figure Z2 depicts various patterns inside of squares the same size as the designated figure Z1, and 8 of them are drawn around the perimeter of the aforementioned designated figure Z1.

Figure 5:
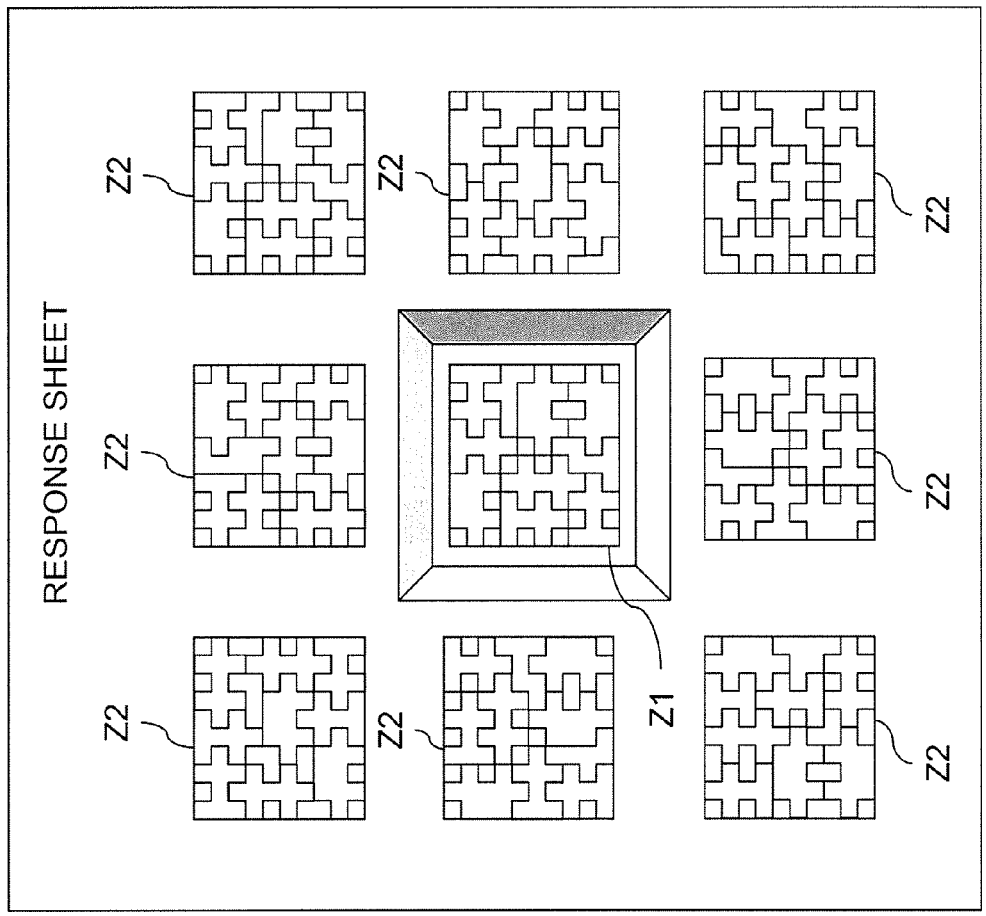
FIG. 5 is a diagram indicating the contents of assignment K2 of the same embodiment.

Meanwhile, as indicated in FIG. 5, the task given in the assignment K2 is to respond with the number of figures among the multiple assignment figures Z2 that match with the aforementioned designated figure Z1 in the same way as in assignment K1, but the aforementioned supplement sheet A is not provided.

In addition, both assignments K1 and K2 are set up with 30 second rest periods after performing the respective tasks above, that is, after the subject completes the tasks, a 30 second rest period is taken, and then the next task is performed.

Then, the results of the subject having performed assignment K1 and assignment K2 were as follows.

Waveforms such as those indicated in FIGS. 8, 11, 14, 17, and 20 were obtained for the light absorbance time sequence data corrected by the baseline correction units 51, 52, 53, 54, and 55; and waveforms such as those indicated in FIGS. 9, 12, 15, 18, and 21 were obtained for changes in the hemoglobin concentration time sequence data derived from these corrected light absorbance time sequence data. As demonstrated from the above, the results obtained by these baseline correction techniques are completely different.

Figure 20:
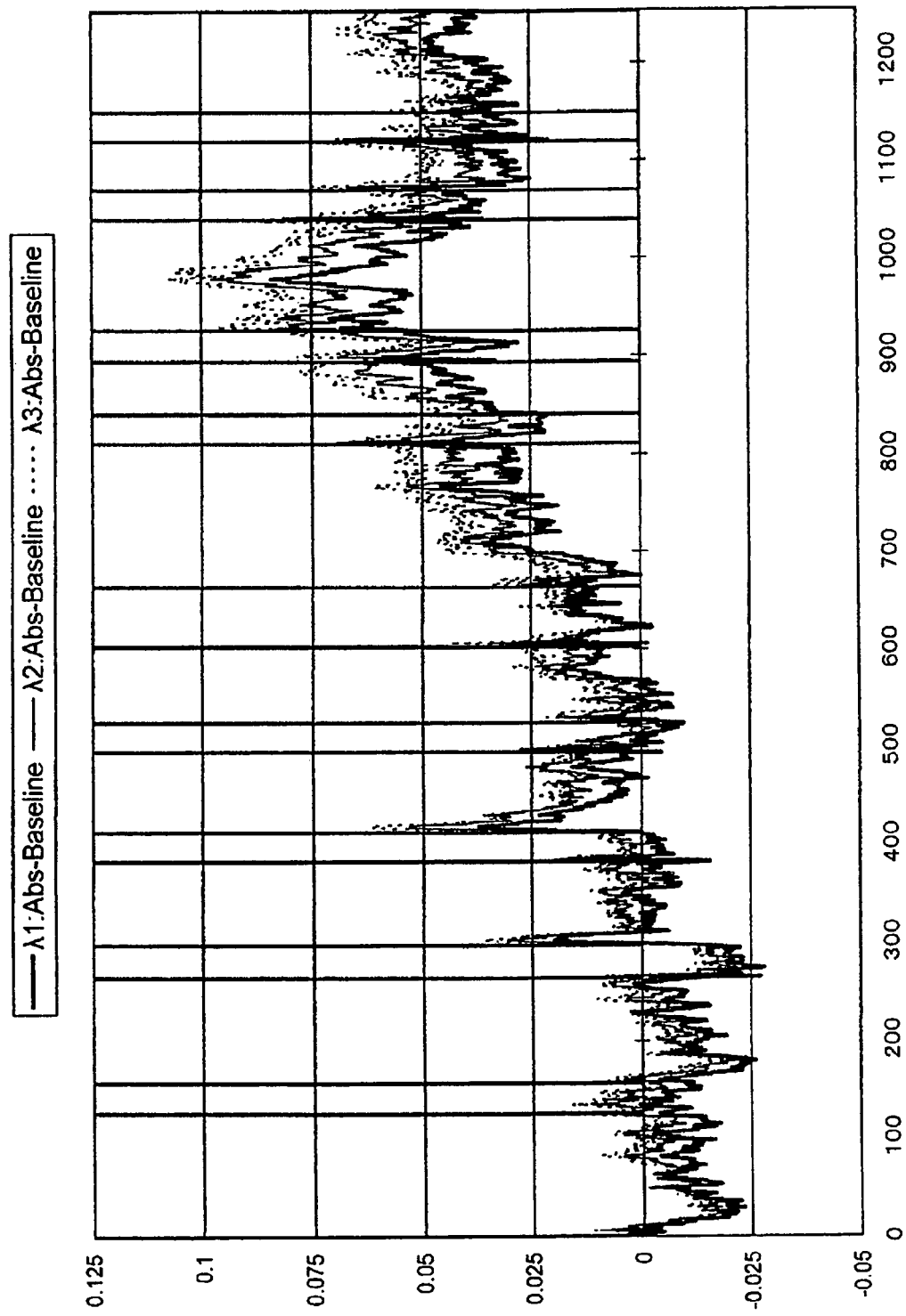
FIG. 20 is a waveform diagram indicating light absorption time sequence data corrected by a baseline correction unit of the same embodiment.
Figure 21:
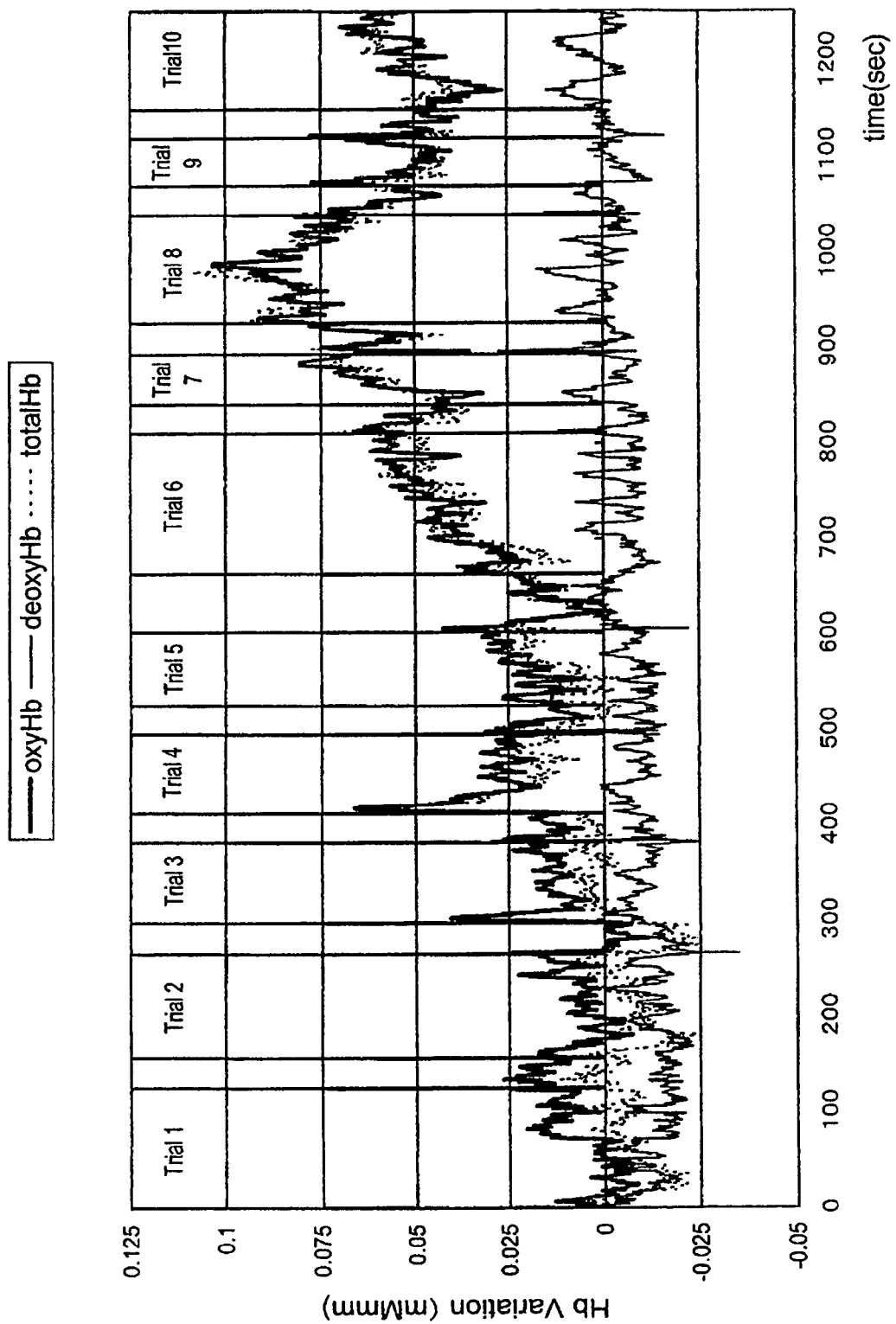
FIG. 21 is a waveform diagram indicating changes in the hemoglobin concentration time sequence data in the same embodiment.

The data obtained by using baseline correction units 51 to 53 to correct the baseline depict waveforms that deviate from the trends shown by the raw light absorbance sequence data and the hemoglobin concentration time sequence data obtained from these (During performance of assignment K2 the overall blood flow rate in the brain was greater than during performance of assignment K1. The extent of reduction of blood flow rate during rests in assignment K2 was smaller than that in assignment K1.), and thus had little validity. In contrast, the light absorbance time sequence data corrected by the baseline correction unit 54 maintained the trends observed in the raw light absorbance time sequence data (FIG. 6) and the light absorbance time sequence data in which only the measurement standard was set up (FIG. 20).

Moreover, the trend of heightened oxyHb concentration during performance of assignment K2 was notably expressed.

When scrutinizing the characteristics of the assignments, the tasks in assignments K1 and K2 require considerable cognitive capacity, and place a large burden on the brain of the subject. For this reason, once elevated, it appears difficult for the blood flow rate to go down (difficult to return to the normal state) during rest periods of about 30 seconds after completing the tasks. Specifically, it appears that determining the baseline data based on the values of light absorbance data during rest is inappropriate. Moreover, because the repeated assignment K2 in the second half required more cognitive capacity than the repeated assignment K1 in the first half, it appears that the characteristics of the background of the hemodynamics caused by psychological states such as tension will be higher when performing assignment K2 than when performing assignment K1. Further, although the assignment K1 and K2 baseline data (background) differed for this subject, such a great difference was not observed in another subject. This is a result that matches the impression stated by this subject that "assignment K2, which did not use supplement sheet A, did not feel that difficult."

Then, when performing assignments K1 and K2 having these characteristics, appropriate measured values were obtained by baseline correction using baseline correction unit 54 that employs different functions to express the baseline data corresponding to the content of the assignment.

EMBODIMENT 2

The assignment K3 given to the subjects in this embodiment gave the task of reading a specified book for one minute, and then resting for one minute after reading for one minute, and this was repeated five times changing the book given each time. Compared to assignments K1 and K2, this assignment K3 did not comprise a task requiring such high cognitive capacity, and after the task, a rest period was given equal in time to that of the task.

In this embodiment, the most suitable measured values could be obtained by correcting the baseline using the baseline correction unit 52 that removes the influence of the increase in blood flow caused by the task at the time of completing one task, that is, at the initial time of rest.

As described in detail above, because the body activity measurement device 1 of the present embodiment can use multiple methods to conduct baseline correction of light absorbance time sequence data, it is possible to correct the light absorbance time sequence data by selecting the appropriate baseline correction unit corresponding to the contents and form of performance of the assignment that the subject P is made to perform. As a result, the time sequence changes of the concentration (amount) of hemoglobin indicating the hemodynamics of the brain can be properly derived, and therefore the brain activity at the time of performing the assignment can be reliably observed.

Further, when correcting light absorbance time sequence data using any of the baseline correction units 51 to 55, corrections are implemented that subtract the baseline data from the light absorbance time sequence data, and therefore it is not necessary to simultaneously set up photometric standards or to provide separate means to set up photometric standards.

In the present embodiment, baseline correction units 51, 52, and 53 were provided as the multiple baseline correction units corresponding to the body activity measurement when repeatedly performing an assignment comprising a task and a rest period, and therefore, when performing the assignment K3 indicated in embodiment 2, or other assignments comprising tasks that place little burden on the subject, suitable baseline correction can be conducted. This is because brain activity when performing these tasks that do not place that great a burden on the subject is more greatly influenced by the hemodynamics corresponding to the cycle of performing the assignment (or the cycle of tasks and rests) than by the psychological state.

Further, by providing the baseline correction unit 54, when continuing on with a different assignment, it is possible to conduct new baseline correction that was not conducted in the past by changing the baseline corresponding to the contents of the assignment (degree of relative difficulty in embodiment 1), and heretofore undiscovered new data can be obtained.

Moreover, in the present embodiment the light absorbance time sequence data in which the baseline was corrected by the baseline correction units 51 to 54 and the hemoglobin concentration time sequence data derived therefrom can be compared with raw light absorbance time sequence data and hemoglobin concentration time sequence data derived by setting up only the measurement standard with the raw light absorbance time sequence data and the baseline correction unit 55, and it is possible to eliminate the corrected data that notably deviates from the trends of the raw light absorbance time sequence data.

The present invention is not limited to the embodiments above.

For example, the embodiments above were configured so that the user determined the optimum baseline correction method from the output results, but a data determination unit may be provided that stores in a specified memory unit existing baseline information related to the assignments and the baseline correction system, and determines the optimum baseline correction method by referring to the stored information.

In addition, the time sequence data generator may also be one that generates time sequence data by digitizing the light absorbance signals and indicating the changes of that time sequence without calculating the light absorbance from the light intensity of each wavelength detected by the detector. In this case, the multiple baseline correction units are configured to correct the baselines of the time sequence data of the light intensity signals. In addition, it may be preferable to provide a hemoglobin concentration time sequence data generator configured such that hemoglobin concentration time sequence data is produced that indicates the time sequence changes of the oxyHb concentration, deoxyHb concentration and totalHb concentration respectively from the time sequence data of the corrected light intensity signals.

Moreover, the baseline correction units are not limited to the embodiments above, and may be of various types such as units in which the baseline data is expressed by a constant function that takes as the constant the value of the time sequence data at, for example, an intermediate time or final time during performance of the assignments, or units expressed by a function of higher degree determined by the values of the time sequence data at multiple time points.

In addition, a baseline correction unit may be provided that removes overall fluctuations of baseline data by using baseline data expressed, not by a function corresponding to the cycle and contents of the assignment, but rather by a spline function that approximates the values of the time sequence data at multiple times of the time sequence data.

In addition, the device may be configured such that baseline correction unit extraction means are provided that extract from the multiple baseline correction units the baseline correction unit corresponding to the assignment that the subject performs, and one of the aforementioned baseline correction units conducts the baseline correction on the time sequence data based on the baseline correction unit extracted by this extraction unit. Further, the baseline correction extraction means may be one that extracts only the unit judged optimum from the characteristics of the assignment, or one that extracts all baseline correction units employed in a multiple candidate baseline system that are judged appropriate. The baseline correction unit extraction means may be configured to extract the baseline correction unit equivalent to a selection signal that the user inputs, or configured to automatically extract the baseline correction unit corresponding to a task based on information input relating to the assignment. In addition to the previously described information relating to the characteristics of the task, raw time sequence data, which is information related to the results obtained by the subject performing the assignment and that has not undergone baseline correction, may be cited as the aforementioned information relating to the assignment. Using this kind of device has little waste and is convenient for the user because only the targeted measured values that are appropriate or are thought to be appropriate corresponding to the assignment are obtained. In this case, an assignment information storage unit is provided that stores in advance information related to assignments by relating the assignment information to one or multiple baseline correction units that employ a baseline correction method suitable for the assignment information or judged suitable from the past data; and the baseline extraction unit may be configured such that the information stored in the assignment information storage unit is compared with the information related to the assignment that has been input, and the corresponding information, or configured such that the assignment information similar to the information relating to the assignment that has been input, is extracted.

The assignment that the subject is made to perform is not limited to those above and may comprise an assignment that includes a task of physical exercise, etc., or an assignment that includes a task that provides a stimulus to the five senses such as, for example, "listening to something" or "looking at something".

The light used for the measurement is not limited to near infrared light, and may be visible light. Moreover, the detection unit may be one that detects the intensity of fluorescent light that exits from the measurement site irradiated with light of a specified wavelength from an irradiation unit.

The body substance is not limited to oxyHb and deoxyHb. Glucose and cytochrome are substances related to the dynamics of blood flow, and any other type of body substance that can be measured by light of a specified wavelength may naturally be used.

Moreover, the device is not limited to measuring the brain, and may measure body activities within the tendons and muscles during movement.

Those skilled in the art will appreciate that various adaptations and modifications of the just-described preferred embodiment can be configured without departing from the scope and spirit of the invention. Therefore, it is to be understood that, within the scope of the amended claims, the invention may be practiced other than as specifically described herein.

The invention claimed is:

1. A body activity measurement device comprising:
   a light irradiation unit configured to irradiate light of a specified wavelength on a specified measurement site of a body of a subject;
   a light detector configured to detect the intensity of the light exiting from the aforementioned measurement site based on the irradiated light of the light irradiation unit;
   a time sequence data generator that, based on the time sequence changes of the intensity of the exiting light that the light detector detects, generates time sequence data suggesting the changes in amount or changes in concentration of a specified body substance pertaining to the body activity; and
   multiple baseline correction units that correct baselines that mutually differ in relation to the aforementioned time sequence data obtained when the aforementioned subject performs specified assignments, configured such that the aforementioned baseline correction of the time sequence data can be conducted using one or multiple baseline correction units corresponding to the assignment performed by the subject.

2. The body activity measurement device according to claim 1 wherein the aforementioned multiple baseline correction units correct by subtracting the baseline data indicating the baseline from the aforementioned time sequence data, and
   the aforementioned baseline data is expressed by a function related to time that refers to all or part of the values of the time sequence data generated by the aforementioned time sequence data generator.

3. The body activity measurement device according to claim 2 wherein, when the subject repeatedly performs the specified assignment, the aforementioned multiple baseline correction units comprise at least a baseline correction unit in which the aforementioned baseline data is expressed by a function referencing the values of the time sequence data of a specified time during performance of the various assignments.

4. The body activity measurement device according to claim 3 wherein the aforementioned specified assignment comprises a specified task and a rest period when that task is not given; and the aforementioned baseline data is expressed by a linear function set up for each task and rest period, and determined by the values of the time sequence data at the initial times of the respective tasks and rest periods, and by the values of the time sequence data at the final times of the respective tasks and rest periods.

5. The body activity measurement device according to claim 3 wherein the aforementioned specified assignment comprises a specified task and a rest period when that task is not given; and the aforementioned baseline data is expressed by a constant function that is set up for each task and rest period, and that takes as a constant the values of the time sequence data at the initial times of the respective tasks and rest periods.

6. The body activity measurement device according to claim 3 wherein the aforementioned specified assignment comprises a specified task and a rest period when that task is not given; and the aforementioned baseline data is expressed by a linear function set up between each specified time of a rest period, and determined by the values of the time sequence data at specified times of specified rest periods, and the values of the time sequence data of specified times of the following rest periods.

7. The body activity measurement device according to claim 2 wherein, when the subject continues to perform assignments with two or more differing contents, the aforementioned multiple baseline correction units comprise at least a baseline correction unit that expresses the aforementioned baseline data with a function that references the values of the time sequence data at specified times during performance of the assignments.

8. The body activity measurement device according to claim 7 wherein the aforementioned baseline data is expressed by a constant function that is set up for each assignment, and that takes as the constant the values of the time sequence data at the initial times of the assignments.

9. The body activity measurement device according to claim 1 wherein baseline correction unit extraction means are provided to extract from the aforementioned multiple baseline correction units the baseline correction units corresponding to the assignment the subject is made to perform, and the time sequence data is corrected by the baseline correction units extracted by this baseline correction unit extraction means.

10. The body activity measurement device according to claim 1 wherein the measurement site is on the brain, and brain activity is measured as the body activity.

11. The body activity measurement device according to claim 1 wherein the light of a specified wavelength that is irradiated by the aforementioned light irradiation unit is near infrared light.

12. The body activity measurement device according to claim 1 wherein the specified body substance participating in the aforementioned body activity is serum, oxyHb and deoxyHb.

13. A body activity measurement system comprising:
a light irradiation unit configured to irradiate light of a specified wavelength on a specified measurement site of the body of a subject to provide a measurement of a characteristic of the body;
a light detector configured to detect the intensity of the light exiting from the aforementioned measurement site based on the irradiated light of the light irradiation unit;
a predetermined assigned task material to require activity by the body of the subject;
a stored table of correction values related to predetermined baseline values associated with the predetermined assigned task;
a time sequence data generator that, based on the time sequence changes of the intensity of the exiting light that the light detector detects, generates time sequence data representative of changes in the characteristics of the body during and after the predetermined assigned task; and
a baseline correction assembly for determining from the time sequence data a baseline value corrected by a correction value obtained from the stored table of correction values appropriate to the body of the subject and the predetermined assigned task.

14. The body activity measurement system of claim 13 wherein the light detection measures oxygenated hemoglobin and deoxygenated hemoglobin of the subject.

15. A body activity measurement device comprising:
a detector unit configured to be operatively connected to a body of a subject for providing measurement signals characteristic of the body during and after a predetermined activity of the subject;
a time sequence generator that, based on the time sequence changes of signals that the detector unit detects, generates time sequence data of the changes in the characteristic of the body during the body activity; and
multiple baseline correction units that correct baselines that mutually differ in relation to the aforementioned time sequence data obtained when the aforementioned subject performs a specified assignment, wherein the aforementioned baseline correction of the time sequence data can be conducted using one or more multiple baseline correction units corresponding to the assignment performed by the subject.

16. The body activity measurement device of claim 15 wherein the detector unit measures the characteristics of the body during the specified assignment and during a subsequent rest period.

17. The body activity measurement device of claim 16 wherein the multiple baseline correction units include correction values related to the specified assignment.

* * * * *